(12) United States Patent
Haq et al.

(10) Patent No.: US 6,284,080 B1
(45) Date of Patent: Sep. 4, 2001

(54) BARRIER METALLIZATION IN CERAMIC SUBSTRATE FOR IMPLANTABLE MEDICAL DEVICES

(75) Inventors: Samuel F. Haq, Mesa; Patrick F. Malone, Phoenix; Donald P. Varner, Tempe, all of AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/626,415

(22) Filed: Jul. 26, 2000

Related U.S. Application Data

(62) Division of application No. 09/282,131, filed on Mar. 31, 1999, now Pat. No. 6,146,743, which is a division of application No. 08/847,906, filed on Apr. 28, 1997, now abandoned.
(60) Provisional application No. 60/038,471, filed on Feb. 21, 1997.

(51) Int. Cl.$^7$ .......................... B32B 31/26; B32B 31/12; H01R 3/10
(52) U.S. Cl. .................... 156/89.16; 156/89.12; 156/89.18; 29/851; 264/620; 174/257
(58) Field of Search .............. 156/89.11, 89.16, 156/89.17, 89.18, 89.19, 89.21, 252, 89.12; 428/210, 901; 29/851, 852; 174/257; 264/620

(56) References Cited

U.S. PATENT DOCUMENTS

| | | |
|---|---|---|
| 4,316,942 | 2/1982 | Kuo ........................................ 428/432 |
| 4,374,382 | 2/1983 | Markowitz ...................... 340/870.01 |
| 4,476,868 | 10/1984 | Thompson ..................... 128/419 PG |
| 4,521,329 | 6/1985 | Siuta et al. ............................ 252/512 |
| 4,556,063 | 12/1985 | Thompson et al. ............ 128/419 PT |
| 4,636,332 | 1/1987 | Craig et al. ........................... 252/514 |
| 4,775,503 | * 10/1988 | Dubuisson . |
| 4,780,248 | 10/1988 | Donohue et al. ..................... 252/518 |
| 4,819,056 | 4/1989 | Palanisamy ............................. 357/80 |
| 4,859,365 | 8/1989 | Peninger ............................... 252/601 |
| 4,910,643 | 3/1990 | Williams ............................... 361/414 |
| 4,961,999 | 10/1990 | Hormadaly ............................ 428/427 |
| 4,982,267 | 1/1991 | Mones et al. ........................... 357/71 |
| 5,011,725 | * 4/1991 | Foster . |
| 5,052,388 | 10/1991 | Sivula et al. ................... 128/419 PG |
| 5,122,302 | 6/1992 | Hormadaly ............................ 252/518 |
| 5,127,404 | 7/1992 | Wyborny et al. ................. 128/419 P |
| 5,162,062 | 11/1992 | Carroll et al. .......................... 148/24 |
| 5,175,609 | 12/1992 | DiGiacomo et al. ................. 257/766 |
| 5,294,567 | 3/1994 | Dorfman et al. ...................... 437/187 |
| 5,303,457 | 4/1994 | Falkner, Jr. et al. ................ 29/25.35 |
| 5,318,820 | 6/1994 | Smith et al. ........................... 428/77 |
| 5,324,370 | 6/1994 | Aoki et al. ............................. 156/64 |
| 5,367,195 | 11/1994 | DiGiacomo et al. ................. 257/767 |
| 5,391,917 | 2/1995 | Gilmour et al. ...................... 257/690 |
| 5,496,619 | 3/1996 | Itagaki et al. ........................ 428/209 |
| 5,782,891 | 7/1998 | Hasslet et al. ......................... 607/36 |
| 5,855,995 | * 1/1999 | Haq et al. .............................. 428/210 |
| 6,041,496 | * 3/2000 | Haq et al. ............................... 29/852 |
| 6,146,743 | * 11/2000 | Haq et al. . |

FOREIGN PATENT DOCUMENTS

| | | | |
|---|---|---|---|
| 0226385 | 6/1987 | (EP) | ................................ C25D/5/10 |
| 0591604 | 4/1994 | (EP) | ................................ H05K/3/46 |

OTHER PUBLICATIONS

Hassler, Beth Anne, "Fast Turnaround Multilayer Cofired Ceramic Motherboard Fabrication" presented to Second Electronic Packaging Materials and Processes Conference in Minneapolis, MN. 10/85, pp. 117–122.

Unknown author, "Method of Curing an Article" published in Research Disclosure Mar. 1984, p. 104.

* cited by examiner

*Primary Examiner*—Curtis Mayes
(74) *Attorney, Agent, or Firm*—Girma Wolde-Michael

(57) ABSTRACT

The present invention relates to multi-layer ceramic packaging of hybrid micro-electronic devices, including those for implantable medical devices. The invention permits size reduction and design simplification in such packaging by eliminating the need for electrolytic or electroless plating, and by eliminating or substantially eliminating the shrinkage variation typically associated with surface metallization techniques.

2 Claims, 15 Drawing Sheets

BARRIER METALLIZATION IN CERAMIC SUBSTRATE FOR IMPLANTABLE MEDICAL DEVICES

This application is a division of prior application Ser. No. 09/282,131 filed Mar. 31, 1999 now U.S. Pat. No. 6,146,793, which claims benefit of Ser. No. 60/038,971 filed Feb. 21, 1997 which is a divisional application of Ser. No. 08/847,906 filed Apr. 28, 1997 now abandoned.

CROSS-REFERENCE TO RELATED APPLICATION

This patent application claims the benefit of U.S. Provisional Patent Appln. Ser. No. 60/038,471 filed Feb. 21, 1997 to Malone et al. entitled "High Temperature Plus (HT+) Multi-Substrate Ceramic Substrate Technology." This patent application also incorporates by reference herein, in its entirety, co-pending U.S. Patent Appln. Ser. No. 08/847,856 filed Apr. 28, 1997 to Haq et al. entitled "Ceramic Substrate for Implantable Medical Devices."

FIELD OF THE INVENTION

This invention relates generally to multi-layer ceramic packaging of hybrid micro-electronic devices, and methods of making and using same.

BACKGROUND OF THE INVENTION

Several methods currently exist for manufacturing ceramic networks or substrates employed in hybrid microelectronic circuits. Current ceramic technologies include so-called High Temperature Co-Fired Ceramic Technology (HTCC), thick film technology, thin film technology and Low Temperature Co-Fired Ceramic technology (LTCC).

In standard HTCC processes, refractory metals such as tungsten or molybdenum are typically employed for conductor material. The typical HTCC product requires either electrolytic or electroless nickel and gold plating. Plating processes increase part costs. Electrolytic plating requires the design of an interconnection scheme of runners called plating bars for tying electrical nodes together and permitting the flow of electrical current required in an electrolytic process. Electrolytic plating also requires complicated, expensive equipment, and often results in increased electrical cross-talk and larger part size. Electroless plating of HTCC networks eliminates the requirement for plating bars, but may result in- gold thickness for wire bonding that are insufficient. Moreover, the electroless plating process commonly employed to manufacture HTCC networks is known to be somewhat unstable in respect of controlling plating thickness.

HTCC networks typically exhibit ceramic shrinkage variation that is excessive for automatic substrate processes or flip chip applications. HTCC does offer the advantage of a product that exhibits high flexural strength. Additionally, HTCC permits leads or seal rings to be brazed directly onto the substrate. This latter advantage is important in respect of some implantable medical devices, where hermetically sealed packages may be required.

Standard thick film processes employ multiple layers of conductor and dielectric material that are applied onto a pre-fired ceramic substrate. This method of manufacturing has been used for many years, and as a result printable dielectrics and metallizations are commercially available. Due to the high cost of precious metal conductor materials, the cost of a device increases as the number of interconnect layers increases. Consequently, as device complexity increases thick film processes become costly. Although thick film metallization systems may be employed at relatively low cost, such systems may suffer from problems such as silver migration. Thin film processes typically require vacuum deposition of a metallization surface layer onto a substrate followed by deposition of a polyimide or similar film thereon, and selective etching of the deposited film to form the desired circuitry pattern.

LTCC is a-variant of conventional thick and thin film processes, where dielectric screen printing is replaced with so-called "green sheets" of dielectric material having via holes filled with gold or silver and conductor layers printed on one or both sides of the sheets. The green sheets are laminated and die-cut into individual networks. The resulting sheets are fired in conventional furnaces at temperatures that typically range between about 800° C. and about 900° C. for periods of time that typically range between about 1 and about 3 hours.

An advantage of the LTCC process is the ability to use standard thick or thin film processing equipment when nickel or gold plating is not required. Unfortunately, the LTCC process commonly results in products having networks and substrates of low flexural strength. LTCC processes may be prohibitively expensive in applications where high reliability is required, such as in implantable medical device applications, because the gold pastes required for such applications are very expensive. Additionally, some LTCC processes have relatively large shrinkage variations associated with outside metallization.

The paper "Fast Turnaround Mutilayer Cofired Ceramic Motherboard Fabrication" by Hassler presented at the Second Electronic Packaging materials and Processes Conference in Minneapolis, Min. in October, 1985, discloses metallized multilayer cofired ceramic packages, where a substrate has external and internal electrically conductive patterns stacked in layers. High purity alumina ceramic separates and insulates the layers while conductive vias interconnect the-layers. Tungsten paste is used to create the conductive patterns and vias. Tungsten and alumina are cofired into a monolithic unit that is strong, hermetic, dimensionally stable and thermally conductive.

European Patent Application No. 93193541.4 to Hormadaly et al. entitled "Via Fill Components" discloses a thick film paste that is especially useful for via fill applications comprising finely divided particles of conductive metal which is not alloyable with silver selected from the group consisting of osmium, ruthenium, iridium, rhodium and mixtures and alloys thereof dispersed in a liquid organic medium. Optionally, a small amount of inorganic binder may be dispersed in the same medium.

European Patent Application No. 86309387.8 to Early entitled "Rhodium Capped Gold IC Metallization" discloses a two layer gold IC metallization process where a first gold metal layer is deposited atop a first barrier layer by electrodeposition, and a second metal layer or cap is deposited by electrodeposition atop the gold layer. After annealing, a dielectric layer is deposited, vias are formed in the dielectric layer, a second barrier layer is deposited, and a rhodium cap is deposited.

Page 104 of the March, 1984 issue of the publication "Research Disclosures" discloses the elimination of nickel/gold plated metallization by co-firing an alloy paste comprising palladium, platinum, rhodium, a binder and a vitreous frit that is screened in the via of the outer sheets of a multi-layer ceramic structure on top of molybdenum.

In addition to the foregoing Hormadaly et al. and Research Disclosure publications, other publications in the same general field include the U.S. Patents listed below in Table 1.

TABLE 1

Prior Art U.S. Patents

| Patent No. | Title |
|---|---|
| 4,316,942 | Thick Film Copper Conductor Circuits |
| 4,512,329 | Copper Conductor Compositions |
| 4,636,332 | Thick Film Conductor Compositions |
| 4,780,248 | Thick Film Conductor Materials |
| 4,819,056 | Hybrid Thick Film Circuit Device |
| 4,859,365 | Conductive Paste Composition |
| 4,910,643 | Thick Film, Multi-Layer, Ceramic Interconnected Circuit Board |
| 4,961,999 | Thermistor Composition |
| 4,982,267 | Integrated Semiconductor Package |
| 5,122,302 | Thick Film NTC Thermistor Compositions |
| 5,162,062 | Method for Making Multilayer Electronic Circuits |
| 5,175,609 | Structure and Method for Corrosion and Stress-Resistant Interconnecting Metallurgy |
| 5,294,567 | Method for Forming Via Holes in Multilayer Circuits |
| 5,303,457 | Method for Packaging Microelectronic Frequency Selection Components |
| 5,318,820 | HTCC/LTCC Use of Multiple Ceramic Tapes in High Rate Production |
| 5,324,370 | Method of Manufacturing a Multi-Layer Ceramic Circuit Board Containing Layers of Reduced Dielectric Constant |
| 5,367,195 | Structure and Method for a Superbarrier Between a Noble and a Non-Noble Metal |
| 5,391,917 | Multiprocessor Module Packaging |
| 5,496,619 | Substrate Formed from Conductive Paste and Insulating Paste |

As those of ordinary skill in the art will appreciate readily upon reading the Summary of the Invention, Detailed Description of the Preferred Embodiments and Claims set forth below, many of the devices and methods disclosed in publications listed above may be modified advantageously by using the teachings of the present invention.

SUMMARY OF THE INVENTION

The present invention relates to multi-layer ceramic packaging of hybrid micro-electronic devices, including those for use in implantable medical devices.

The present invention permits size reduction and design simplification in such packaging by eliminating the need for electrolytic or electroless plating, and by eliminating or substantially eliminating the shrinkage variation typically associated with surface metallization techniques. The present invention also provides a ceramic substrate where the number and topology of electrical interconnections or interconnects is simplified and reduced, and is particularly well adapted to flip chip applications because it permits surface metallization shrinkage variation to be eliminated or substantially eliminated. Post-firing printing and component placement are aided in the present invention by the external vias not "posting," or having protrusions extending above the top surface of the ceramic substrate after the high-temperature or subsequent firing steps have been completed.

In a ceramic substrate of the present invention, external vias most preferably comprise ruthenium and ceramic and are disposed between internal metallization layers formed most preferably of tungsten or molybdenum, and external surface thick film layers.

In a preferred method of making a ceramic substrate of the present invention, the substrate is fired in a high-temperature firing step at high temperatures in a reducing atmosphere, a thick film external surface layer is applied onto the top or bottom surfaces of the substrate, the substrate is fired in a low-temperature firing step in an inert atmosphere at low temperatures, and finally the substrate is fired at low temperatures in an air atmosphere.

Other objects, features and advantages of the present invention will become apparent upon referring to the appended drawings, detailed description of the preferred embodiments and the claims.

DETAILED DESCRIPTION OF THE PREFERRED EMBODIMENTS

The term "high temperature" as used in the specification and claims hereof means temperatures ranging between about 1400° C. and about 1800° C.

The term "low temperature" as used in the specification and claims hereof means temperatures ranging between about 600° C. and about 1000° C.

The term "layer" means a single sheet of unfired or fired green tape or similar material containing ceramic.

The term "reducing atmosphere" means an atmosphere that includes sufficient reducing gaseous substances such as hydrogen, other suitable gaseous substances, or combinations or mixtures thereof, capable of providing electrons readily, where the reducing gaseous substance surrounds the ceramic substrate, ceramic layer, or metallization layer of the present invention, and the reducing gaseous substance is present in sufficient quantities to prevent or impede, or substantially prevent or impede, the oxidation of one or more selected components of the present invention during a high temperature or low temperature firing process.

The term "inert atmosphere" means an atmosphere that includes sufficient inert, non-reactive gaseous substances such as nitrogen, carbon dioxide, argon, helium or any other suitable gas, or combinations or mixtures thereof, where the inert gaseous substance surrounds the ceramic substrate, ceramic layer, or metallization layer of the present invention, and the inert gaseous substance is present in sufficient quantities to prevent or impede, or substantially prevent or impede, the chemical reaction of one or more selected components of the present invention during a high temperature or a low temperature firing or firing process.

The term "co-firing" means a process of heating, sintering or firing a ceramic substrate comprising a plurality of stacked individual ceramic layers, where each layer has vias or metallization circuitry patterns formed thereupon or therein, and the vias or patterns are disposed on the individual layers thereof.

The terms "firing," "heating" and "sintering" are synonymous.

The term "refractory metal" means a metal such as iridium, molybdenum, osmium, palladium, platinum, rhenium, rhodium, ruthenium, technetium, tungsten, and alloys, mixtures or combinations thereof, and other highly electrically conductive metals known to resist melting at high temperatures.

The term "circuitry pattern" includes within its scope patterns or layers formed of thin film or thick film pastes, inks or other materials suitable for forming electrically conductive, deposited, imprinted, optically projected or chemically formed surface pathways in hybrid electronic devices.

The term "trimming" means cutting to a desired shape a laminated, unfired, stacked substrate, and specifically does not refer to the "trimming" of resistor values in semiconductor or hybrid electronic applications.

Figure 1:
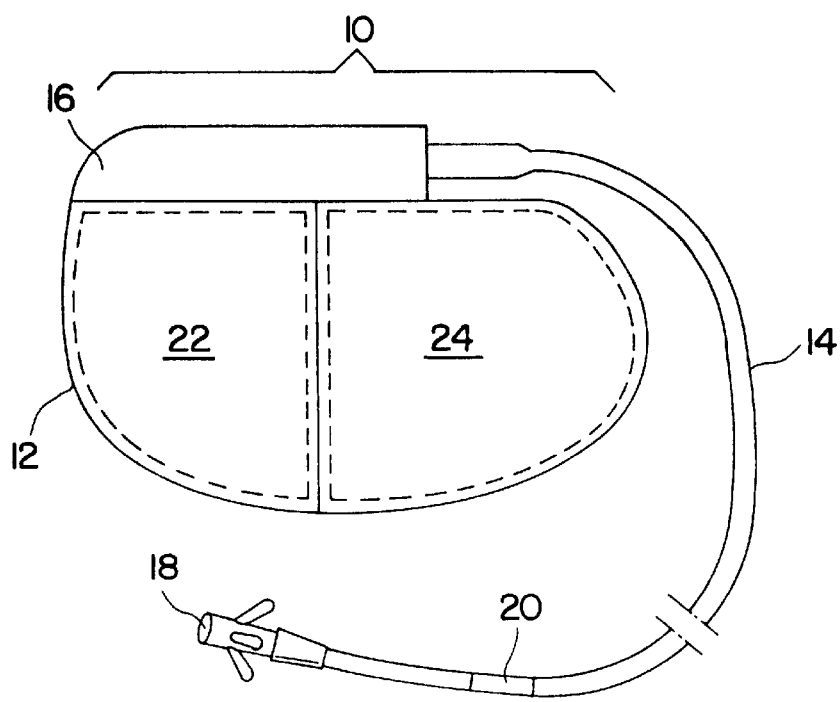
FIG. 1 shows an implantable medical device such as a pacemaker constructed in accordance with one embodiment of the present invention.

FIG. 1 shows implantable medical device pacemaker system 10 constructed in accordance with one embodiment of the present invention. In the embodiment of the present invention illustrated in FIG. 1, implantable medical device 10 is a pacemaker system. The present invention includes within its scope, however, many different types of implantable medical devices such as pacemaker -cardio- defibrillators (PCDs), defibrillators, implantable cardio- defibrillators (ICDs), implantable neuorological stimulators, and other types of implantable medical devices, and is not limited to pacemakers only.

Pacemaker system 10 in FIG. 1 includes a pulse generator housed within a hermetic enclosure 12, and a flexible, elongate lead 14 coupled to a header or connector block assembly 16 attached or coupled to pulse generator enclosure 12. Enclosure 12 is preferably formed of titanium or any other suitable biocompatible material or metal. Header 16 is preferably formed of polyurethane or any other suitable biocompatible material or metal. In accordance with conventional practice, lead 14 comprises one or more electrical conductors insulated with a flexible outer sheath formed of biocompatible silastic, silicone rubber, polyurethane or the like. Lead 14 generally has one or more electrodes disposed at or near the distal end thereof. FIG. 1 shows lead 14 as a bipolar lead having tip electrode 18 and ring electrode 20. Other types of leads such as unipolar leads may be employed in conjunction with the present invention.

Header 16 encases one or more hermetic feedthrough elements (not shown in the Figures) for enabling electrical signals to be communicated between the conductors of lead 14 and electronic stimulation and control circuitry 22 disposed within hermetic enclosure 12. Also disposed within hermetic enclosure 12 is a battery 24 for providing power to the various electronic components of pacemaker system 10.

Figure 2:
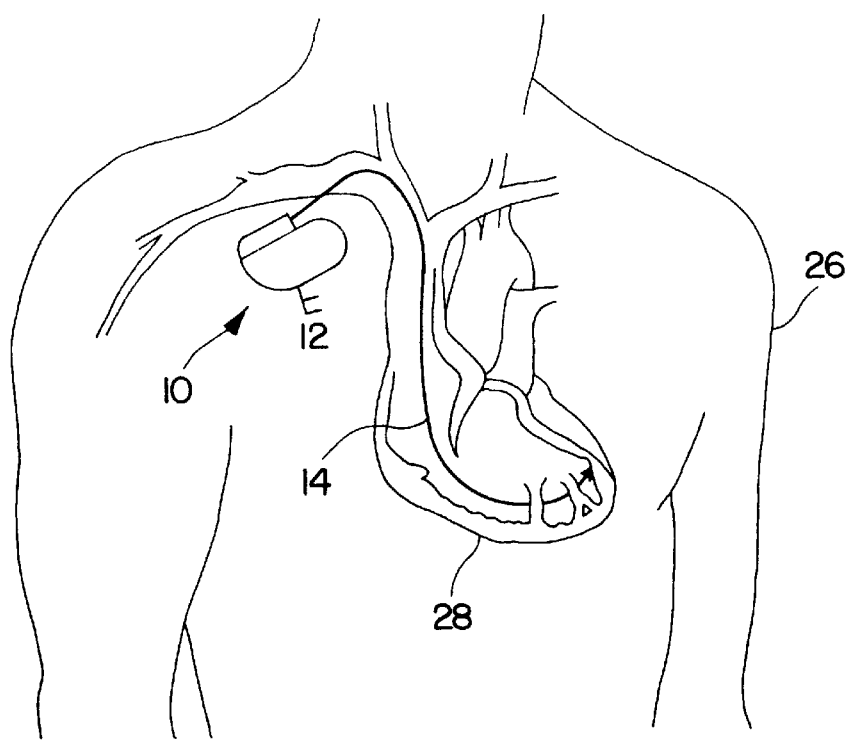
FIG. 2 shows the implantable medical device of FIG. 1 implanted in a human being.

FIG. 2 shows a conventional lateral transvenous implantation of pacemaker system 10 within the body of patient 26. Hermetic enclosure 12 is disposed within a small subcutaneous pocket inferior to the patient's clavicle. Lead 14 extends transvenously from enclosure 12 such that its distal end is disposed within heart 28 of patient 26.

Figure 3:
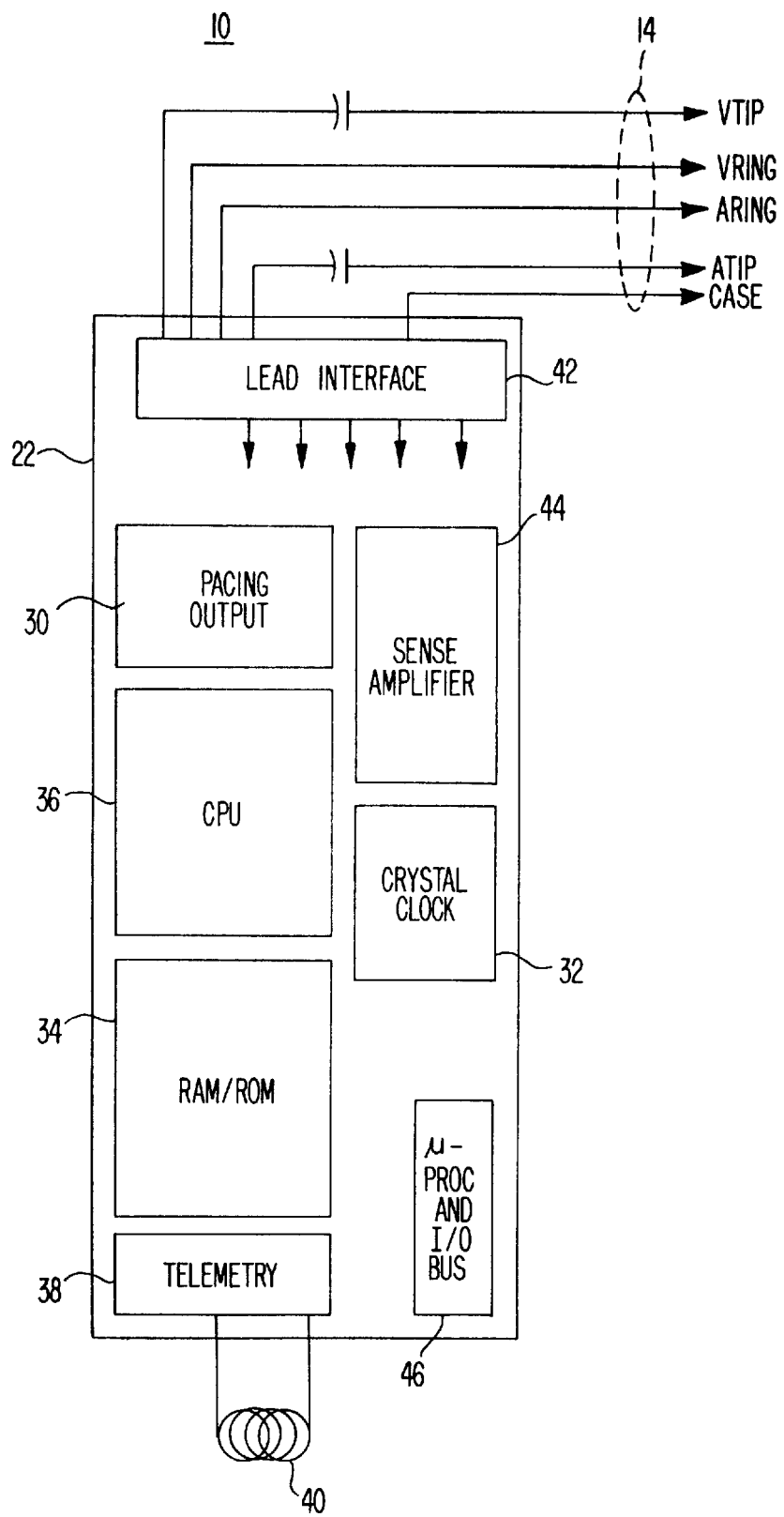
FIG. 3 shows a functional block diagram corresponding to the pacemaker circuitry of the pacemaker system of FIG. 1.

FIG. 3 shows a functional block diagram of pacemaker system 10 having one embodiment of electronic stimulation and control circuit 22 for controlling pacing and sensing functions. Stimulation and control circuit 22 may be of conventional design such as that disclosed in U.S. Pat. No. 5,052,388 to Sivula et al., entitled "Method and Apparatus for Implementing Activity Sensing in a Pulse Generator", which patent is hereby incorporated by reference herein in its entirety. To the extent certain components of pacemaker system 10 are conventional in their design and operation, those components are not described here in great detail as the design and implementation of such components is well known to those of ordinary skill in the art. For example, stimulation and control circuit 22 in FIG. 3 includes stimulating pulse output circuitry or pacing output circuit 30, crystal clock or oscillator 32, random-access memory and read-only memory (RAM/ROM) unit 34, telemetry unit 38, lead interface unit 42 and central processing unit (CPU) 36, all of which are well-known in the art.

Pacemaker system 10 includes intermal communication and telemetry circuit 38 that permits system 10 to communicate with an external programming and control unit that is not shown in the Figures. Associated with communication circuit 38 is radio-frequency antenna 40 for facilitating the receipt and transmission of radio-frequency signals, in accordance with conventional practice and as exemplified by the teachings of U.S. Pat. No. 4,374,382 to Markowitz, entitled "Marker Channel Telemetry System for a Medical Device," U.S. Pat. No. 5,127,404 to Wyborny et al., entitled "Telemetry Format for Implanted Medical Device," and U.S. Pat. No. 4,556,063 to Thompson et al., entitled "Telemetry System for a Medical Device." The foregoing '382, '404 and '063 patents are hereby incorporated by reference herein in their respective entireties.

In one embodiment of the present invention, CPU 36 is a custom microprocessor adapted to fetch and execute instructions stored in RAM/ROM unit 34 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of CPU 36. Furthermore, while we describe the present invention here in the context of an implantable pacemaker system, it is contemplated that the present invention may find beneficial application in implantable medical device systems other than pacemakers such as implantable defibrillators, tachycardia conversion devices, as well as in a wide range of devices not having medical applications.

FIG. 3 further shows stimulation and control circuit 22 coupled to one or more leads 14 that upon implantation extend transvenously between the implant site of pulse generator system 10 and heart 28. Physical connections between lead 14 and the various internal components of circuitry 22 are established and facilitated by conventional connector block assembly 16 shown in FIG. 2. Electrical connections between the conductor or conductors of lead 14 and stimulation and control circuit 22 are established and facilitated by lead interface circuit 42.

Circuit 42 typically functions in a multiplexer-like manner to selectively and dynamically establish electrical connections between and to various conductors in leads 14. For example, electrical connections to atrial tip or ring electrode conductors ATIP and ARING, or ventricular tip or ring electrode conductors VTIP and VRING, may be established through lead 14 by lead interface circuit 42.

For the sake of clarity specific connections between the conductors of lead 14 and the various components of stimulation and control circuitry 22 are not shown in FIG. 3. Those of skill in the art will understand, however, that conductors in lead 14 must be coupled directly or indirectly to sense amplifier circuit 44 and stimulating pulse output circuit 30 to permit the routing of sensed cardiac electrical signals to sensing circuit 44, and the delivery of stimulating pulses to cardiac tissue via lead 14.

Stimulation and control circuit 22 contains central processing unit (CPU) 36, which may comprise an off-the-shelf programmable microprocessor or microcontroller. In a preferred embodiment of the present invention, CPU 36 is a custom integrated circuit. Although specific connections between CPU 36 and other components of stimulation and control circuit 22 are not shown in FIG. 3, CPU 36 controls the timed operation of stimulating pulse output circuit 30 and sense amplifier circuit 44 under the control of programming stored in RAM/ROM unit 34.

Crystal oscillator or clock 32 provides main timing clock signals to stimulation and control circuit 22, and is most preferably a 32,768-Hz crystal-controlled oscillator. The specific lines over which clocking signals are provided to the various timing components of stimulation and control circuitry 22 such as CPU 36 are omitted from FIG. 3 for the sake of clarity.

Other interconnections between the individual components of stimulation and control circuit 22 are represented by microprocessor and I/O bus block 46 in FIG. 3. For example, a connection between CPU 36 and pacing output circuit 30 is preferred such that CPU 36 provides triggering or inhibiting signals to output circuit 30 for controlling the delivery of stimulating pulses to heart 28. For the sake of clarity, those interconnections are not shown in FIG. 3.

The various electrical and electronic components of pacemaker system 10 shown in FIG. 3 are powered electrically by battery 24 (shown in FIG. 1, but not shown in FIG. 3). As depicted in FIG. 1, battery 24 is contained within hermetic enclosure 12 of pacemaker system 10. FIGS. 1 and 2 do not show the specific connections between battery 24 and other components of pacemaker system 10.

Stimulating pulse output circuit 30 generates cardiac stimuli in response to control signals originating in CPU 36, and may be of the type disclosed in U.S. Pat. No. 4,476,868 to Thompson, entitled "Body Stimulator Output Circuit," which patent is hereby incorporated by reference herein in its entirety. Many other types of pacing output circuits are suitable when practicing the present invention.

Sense amplifier circuit 44 receives electrical cardiac signals from lead 14 and processes those signals to derive event-indicating signals that mark the occurrence of specific cardiac electrical events such as atrial contractions (P-waves) and ventricular contractions (R-waves). Those event-indicating signals are provided to CPU 36 for use in controlling the synchronous stimulating operations of pacemaker system 10. Additionally, the event-indicating signals may be communicated by uplink RF transmission to an external programming unit for visual display to a physician.

Pacemaker system 10 may include numerous other components and subsystems such as, for example, activity sensors and associated circuitry. The presence or absence of those additional components in pacemaker system 10, however, is not highly pertinent to the present invention.

Figure 4:
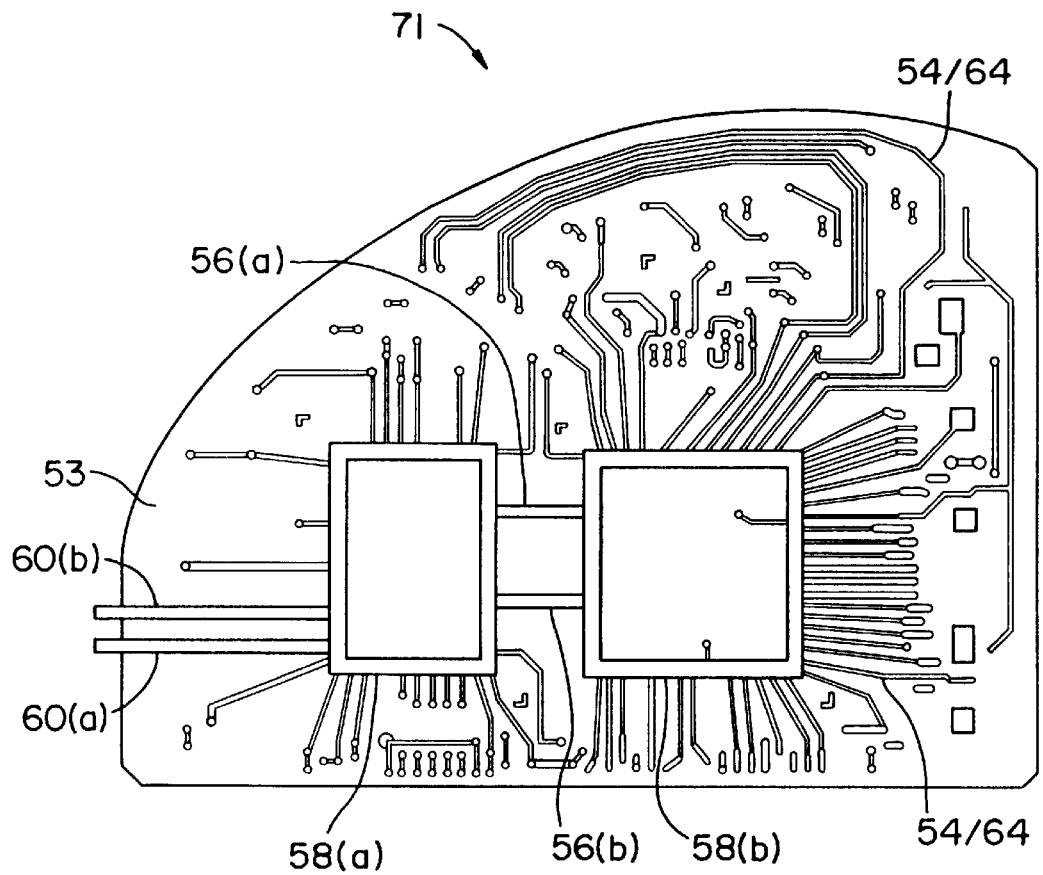
FIG. 4 shows a conventional, prior art metallization layer disposed on the surface of an internal ceramic layer prior to an electrolytic plating step.

FIG. 4 shows a conventional, prior art metallization pattern disposed on top surface 53 of internal layer 71 prior to an electrolytic plating step. Internal layer 71 is formed primarily of ceramic. Most or all conductors 54 are electrically shorted together by extending several plating runners 56(a) and 56(b) to metal frames 58(a), and 58(b) near the center of top surface 53 of ceramic layer 71.

One or more conductors, 60(a) or 60(b) extend to the side of layer 71 for establishing mechanical and electrical connection to an external electrolytic plating rack. After the electrolytic plating step has been completed, a laser scribing step is performed around the perimeter of frames 58(a) and 58(b) to electrically open selected metal conductors. Plating runners 56(a) and 56(b) on top surface 52 occupy valuable ceramic layer surface area and also contribute to electrical noise or cross-talk.

The electrolytic plating process used to form ceramic layer 71 shown in FIG. 4 requires several different steps, including: (a) an edge termination step; (b) a first nickel plating step; (c) a nickel sintering step; (d) a second nickel plating step; (e) a gold plating step; (f) an edge grinding step; and (g) laser scribing step. Those of skill in the art will now appreciate that the electrolytic plating process is capital intensive, time consuming and lengthy. Moreover, electrolytic plating requires the use of several toxic or hazardous chemicals that must be handled with care and disposed of in accordance with complicated federal regulations.

Figure 5:
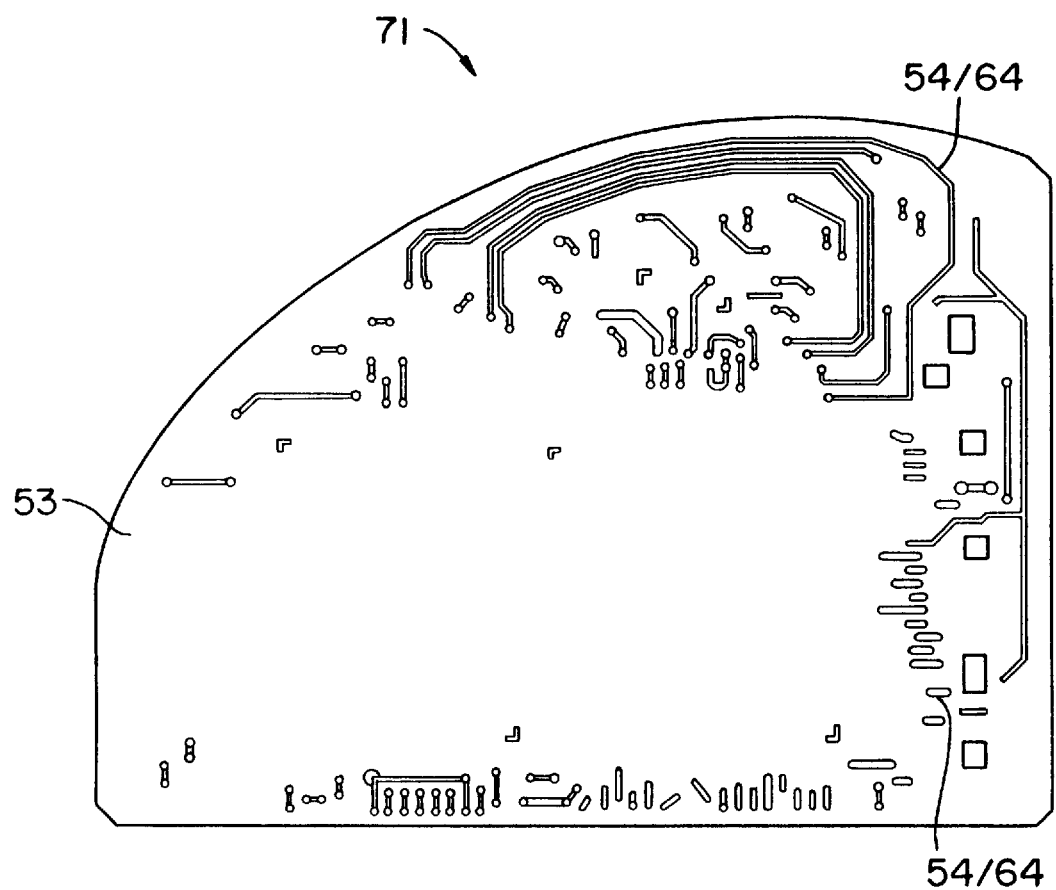
FIG. 5 shows a metallization layer disposed on the surface of one embodiment of an internal ceramic layer of the present invention.

FIG. 5 shows one embodiment of a metallization pattern disposed on top surface 53 of internal layer 71 employed in ceramic substrate 50 of the present invention. Note that plating runners 56(a) and 56(b) and frames 58(a) and 58(b) of layer 71 of FIG. 4 are not present in ceramic layer 71 of the present invention shown in FIG. 5. The process and apparatus of the present invention eliminate entirely the need for electrolytic or electroless plating, and all steps associated therewith, resulting in considerable cost, labor and capital equipment savings.

Another advantage provided by the present invention is the additional surface area that becomes available on surfaces 51, 52 or 53 of ceramic layers 71 and 74 that is generally not available in ceramic substrates known in the prior art. Additionally, improved electrical isolation of certain signals is achieved in the ceramic substrates of the present invention.

In the present invention, certain aspects of HTCC technology are combined with certain aspects of thin or thick film technology to produce a novel ceramic substrate finding particularly efficacious application in the field of electronic hybrid circuits.

Figure 6:
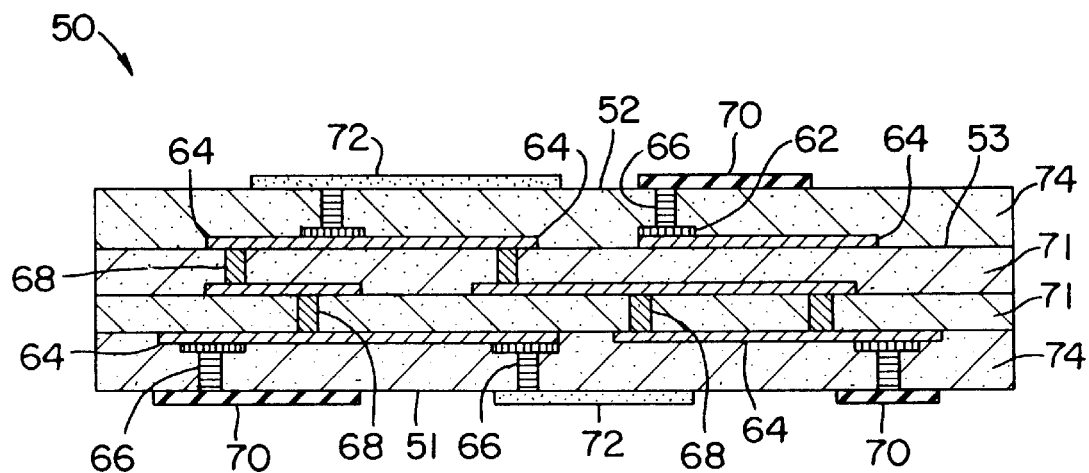
FIG. 6 shows a cross-sectional schematic illustration of one embodiment of the ceramic substrate of the present invention.

FIG. 6 shows a cross-sectional schematic illustration of one embodiment of the ceramic substrate of the present invention. Fourteen or more individual ceramic layers 71 and 74 may be stacked to form a ceramic substrate 50 of the present invention. At least three layers and less than thirteen layers are stacked atop one another in preferred embodiments of substrate 50. Mechanical integrity is imparted to substrate 50 by each of layers 71 or 74.

Internal layers 71 are sandwiched between external layers 74. Bottom surface 51 forms the outer surface of one of external layers 74. Top surface 52 forms the outer surface of the other of external layers 74. Surface 53 forms the top surface of internal layer 71. The external via paste employed to form external vias 66 most preferably differs in composition from that of the internal via paste employed to form internal vias 68. Likewise, the internal paste employed to form internal metallization layers 64 most preferably differs in composition from that of the intermediate paste employed to form intermediate metallization layers 62.

In preferred embodiments of the present invention, tungsten or molybdenum, or alloys, mixtures or combinations thereof, are used in the internal paste from which internal metallization layers 64 are formed owing to their relatively low cost and high electrical conductivity. In the present invention, tungsten and molybdenum may not be employed to form external metallization layers 70 or 72 in substrate 50. In preferred embodiments of the present invention, ruthenium and other relatively exotic metals are employed sparingly owing to their higher cost and generally decreased electrical conductivity and availability respecting tungsten and molybdenum. If cost, availability, and electrical resistance are not important considerations in a product made in accordance with the teachings of the present invention, tungsten and molybdenum may be eliminated from the pastes for forming internal vias 68 or internal metallization layers 64, and ruthenium or other suitable metals such as rhodium, osmium, iridium, palladium, titanium and platinum, or alloys, mixtures or combinations thereof, may be employed in their stead.

Multiple discrete and overlying external metallization layers 70 and 72 of FIG. 6 may be printed on or otherwise applied to upper surface 52 or lower surface 51. In preferred embodiments of the present invention, external metallization layers 70 and 72 are thin or thick film solderable metallization layers or thin or thick film wirebondable metallization layers. External metallization layers 70 and 72 are most preferably formed of an external paste comprising gold, platinum, palladium or silver, or alloys, mixtures or combinations thereof, and are less preferably formed of copper, nickel or alloys or combinations thereof.

Following the high-temperature firing step of the present invention, thin or thick film electrical or electronic components such as conductors, resistors, capacitors and inductors may be printed, vapor deposited, photo-imageably deposited or otherwise applied on top of external metallization layers or circuitry patterns 70 and 72 using methods well known to those skilled in the art. Internal metallization layers 64 of FIG. 6 are most preferably formed of n internal paste comprising molybdenum or tungsten, or alloys, mixtures or combinations thereof. Other, less preferred pastes comprising ruthenium, rhodium, osmium, iridium, palladium, titanium or platinum, or alloys, mixtures or combinations thereof, may also be employed to form the internal pastes of the present invention.

Intermediate metallization layer 62 is not required in substrate 50 of the present invention, especially when substrate 50 is subjected one time only to the high temperature firing step. If substrate 50 is subjected to more than one high temperature firing step, then intermediate metallization layer 62 is preferred and beneficial.

It was discovered that when a substrate of the present invention that does not contain an intermediate metallization layer is fired at high temperatures more than one time, significant amounts of metal contained in internal metallization layers located near external vias migrate to the external vias. For example, it was discovered that after two firings at high temperatures, substrates of the present invention not containing intermediate metallization layers exhibited increases in electrical resistance of between about 20% and 30% relative to similar substrates fired one time at high temperature. After three high temperature firings, open circuits were observed to occur in such substrates. Examination of those substrates under high magnification showed that the increases in resistance and open circuit conditions were caused by such large amounts of internal metallization flowing to the external vias such that excessive thinning of, and even breaks in, the external via/internal metallization layer interface occurred.

To solve the problem posed by increases in resistance and the flow of internal metallization to external vias during multiple firings of substrate 50, intermediate metallization layer 62 or the "catch pad" of the present invention was developed. It was discovered that intermediate metallization layer 62 or the "catch pad" of the present invention inhibits or prevents the migration of metal from internal metallization layers 64 to external vias 66. The inventors speculate that the mechanism by which intermediate metallization layer 62 may prevent or inhibit such metal migration could relate to layer 62 acting as a sacrificial layer for providing metal to external via 66, while metal from internal metallization layer 64 remains in place and does not migrate through the barrier formed by intermediate layer 64. Regardless of the mechanism by which layer 62 provides its results, it was discovered that those results were indeed beneficial.

Intermediate metallization layers 62 of FIG. 6 are most preferably formed of an intermediate paste comprising a mixture of high temperature tungsten and ruthenium powders. Up to about 30% by weight ceramic powder may be included in the intermediate paste and layer 62 of the present invention. The intermediate paste from which layer 62 is formed most preferably comprises a mixture of the metals employed to form internal metallization layer 64 and external via 66. For example, in a preferred embodiment of the present invention, external via 66 contains ruthenium, internal metallization layer 64 contains tungsten, and intermediate metallization layer 62 contains a mixture of tungsten and ruthenium.

If metals other than ruthenium, tungsten and molybdenum are employed to form the intermediate paste of the present invention, the composition of the intermediate paste should most preferably be an alloy, mixture or combination of the metals contained in external via 66 and internal metallization layer 64. A preferred weight percent ratio of the metal present in internal metallization layer 64 to the metal present in external via 66 is about 70/30. Other weight percent ratios of those metals may less preferably be employed in the intermediate paste of the present invention, such as weight percent ratios of about 10/90, about 20/80, 30/70, about 40/60, about 50/50, about 60/40, about 80/20, and about 90/10 of the metal present in internal metallization layer 64 to the metal present external via 66. Depending on the particular alloy, mixture or combination formulation selected for the intermediate paste of the present invention, it may also be desirable to adjust or change the amount of organic material present in the paste medium.

Figure 15:
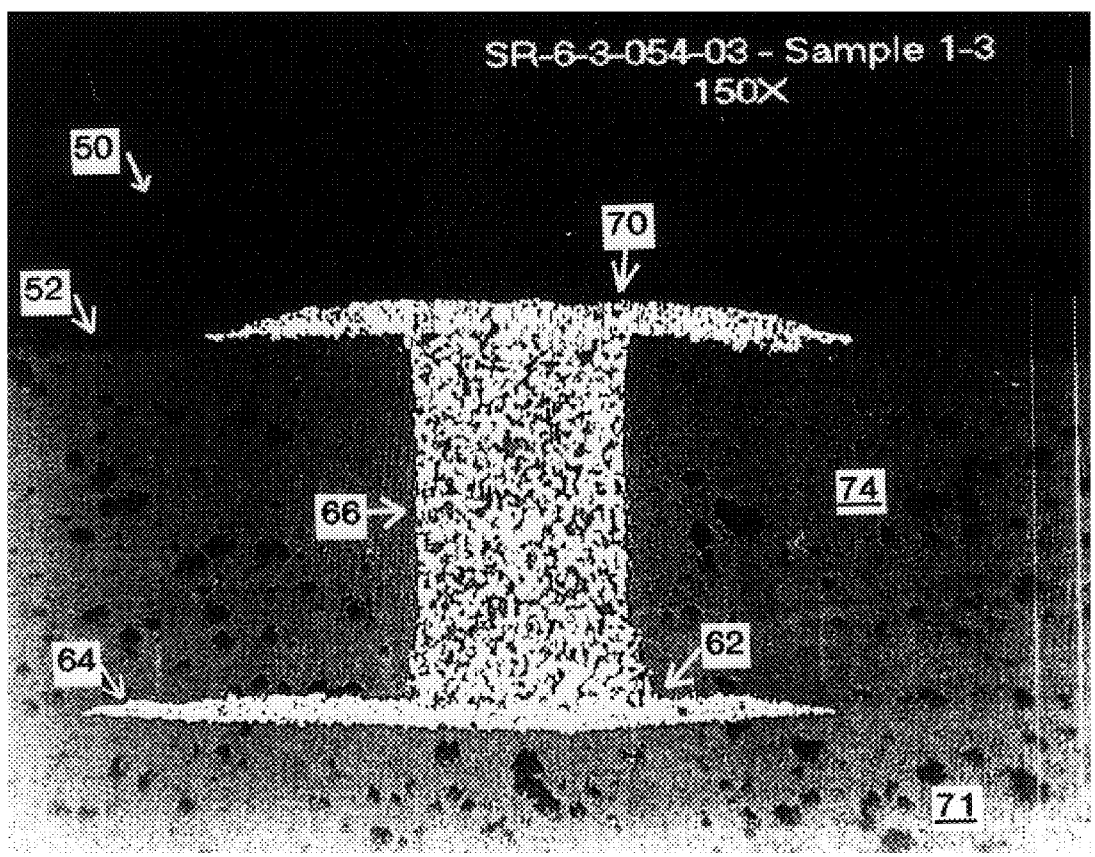
FIG. 15 shows a cross-sectional view of another embodiment of the external via and intermediate metallization layer of the present invention after firing in a reducing atmosphere at high temperature.

FIG. 15 shows a cross-sectional view of external via 66 and intermediate metallization layer 62 of the present invention after substrate 50 has been fired once in a reducing atmosphere at high temperature. In FIG. 15, catch pad or layer 62 is interposed between external via 66 and internal metallization layer 64. FIG. 15 shows that layer 62 has prevented the migration of refractory metal from layer 62 to external via 66 after substrate 50 has been fired once in a reducing atmosphere at high temperatures.

Figure 16:
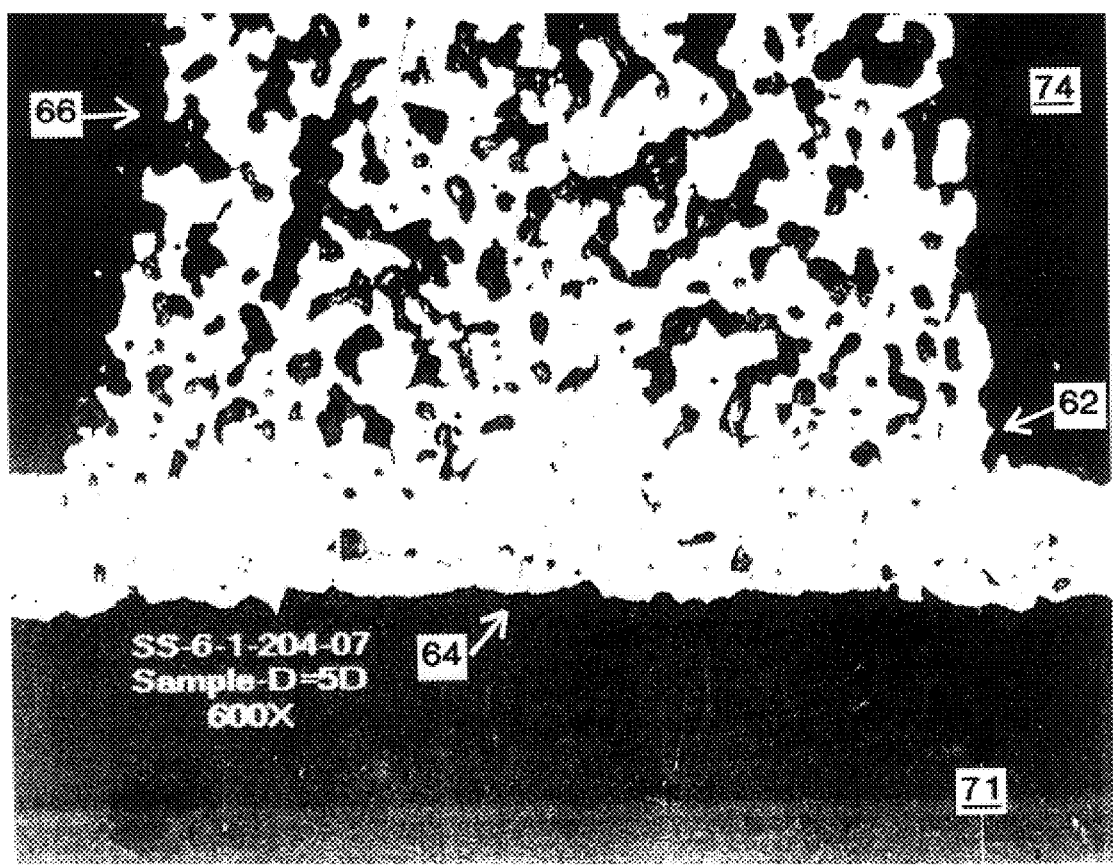
FIG. 16 shows a cross-sectional, highly-magnified view of the external via and intermediate metallization layer of the present invention after firing in a reducing atmosphere at high temperature.

FIG. 16 shows a cross-sectional, highly-magnified view of the right-hand, lower portion of external via 66 and intermediate metallization layer 62 shown in FIG. 15, but after five firings at high temperature. FIG. 16 confirms that the migration of refractory metal from internal layer 64 to external via 66 has been prevented by intermediate metallization layer 64.

In a preferred embodiment of the present invention, an external via paste comprising ruthenium and pre-milled ceramic powder is employed to form external vias 66, which are disposed between internal metallization layers 62 and intermediate metallization layers 64, and upper surface 52 or lower surface 51 (or external metallization layers 70 or 72). A preferred method of making the pre-milled ceramic powder of the external via paste of the present invention is described in detail below.

The ceramic powder component of the external via paste acts as an inorganic binder and also provides substantial shrinkage match between external vias 66 and corresponding upper surface 52 or lower surface 51, such that resulting fired external vias 66 do not protrude substantially above or sink substantially below upper surface 52 or lower surface 51. The ceramic powder component also improves the degree of adhesion between the ceramic forminq the substrate itself and external via 66, thereby ensuring the formation of an hermetic seal in ceramic substrate 50. This hermetic seal inhibits or prevents internal metallization layers 64 from becoming oxidized when substrate 50 is air-fired during one method of the present invention.

Figure 7:
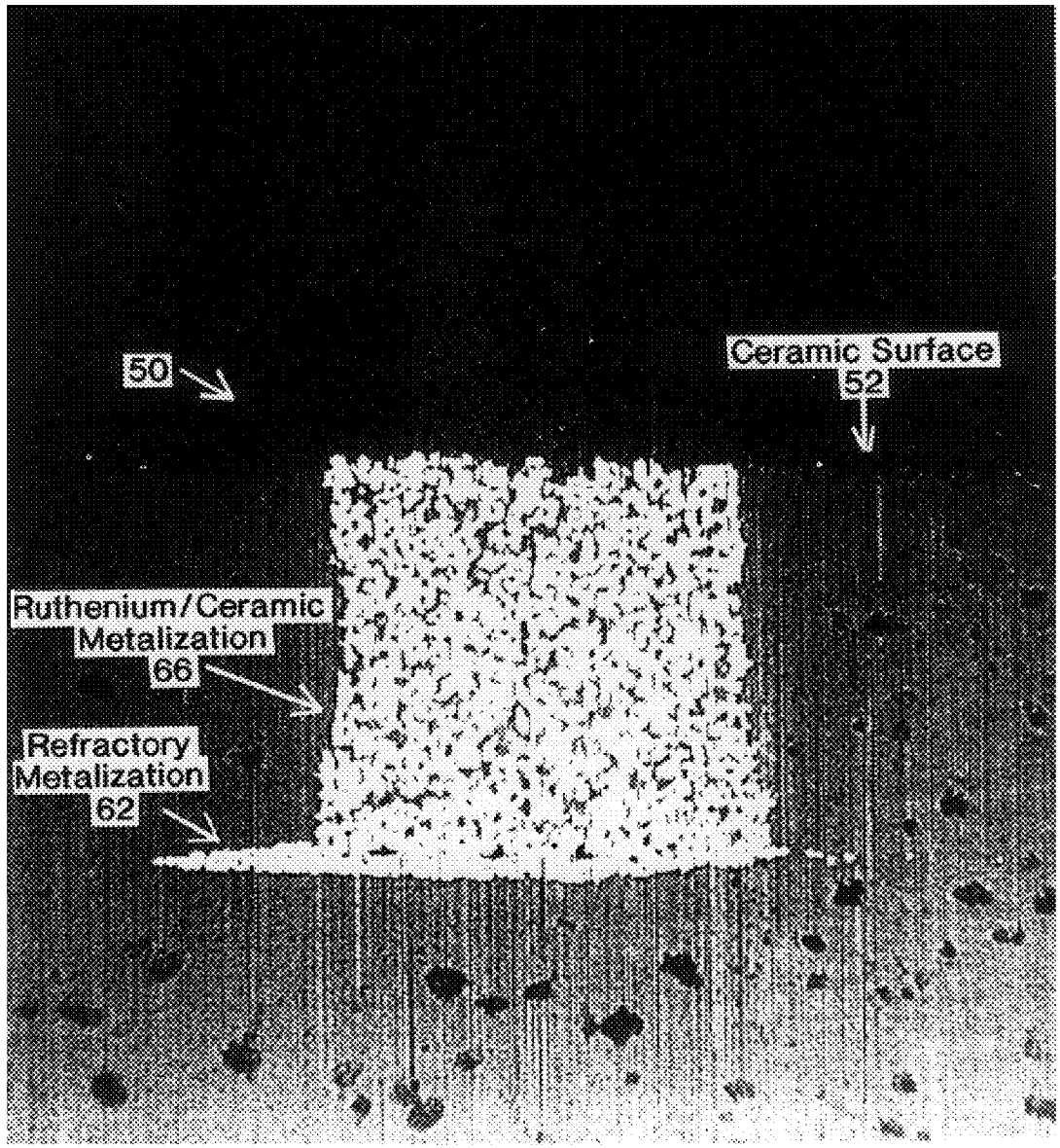
FIG. 7 shows a cross-sectional view of one embodiment of the external via of the present invention after it has been fired in a reducing atmosphere at high temperature.

FIG. 7 shows a cross-sectional view of one embodiment of external via 66 of the present invention after it has been fired in a reducing atmosphere at high temperature in the high-temperature firing step of the present invention. Due to the addition of high temperature ceramic powder to the external via paste, the shrinkage of external via 66 closely matches that of surrounding external ceramic layer 74. As a result, external via 66 does not protrude above upper surface 52 of ceramic layer 74, and a high degree of adhesion develops between external via 66 and the surrounding ceramic walls of layer 74. It is important that the height of external vias 66 after firing be controlled carefully to permit accurate post-firing printing of external metallization layers 70 or 72.

Figure 8:
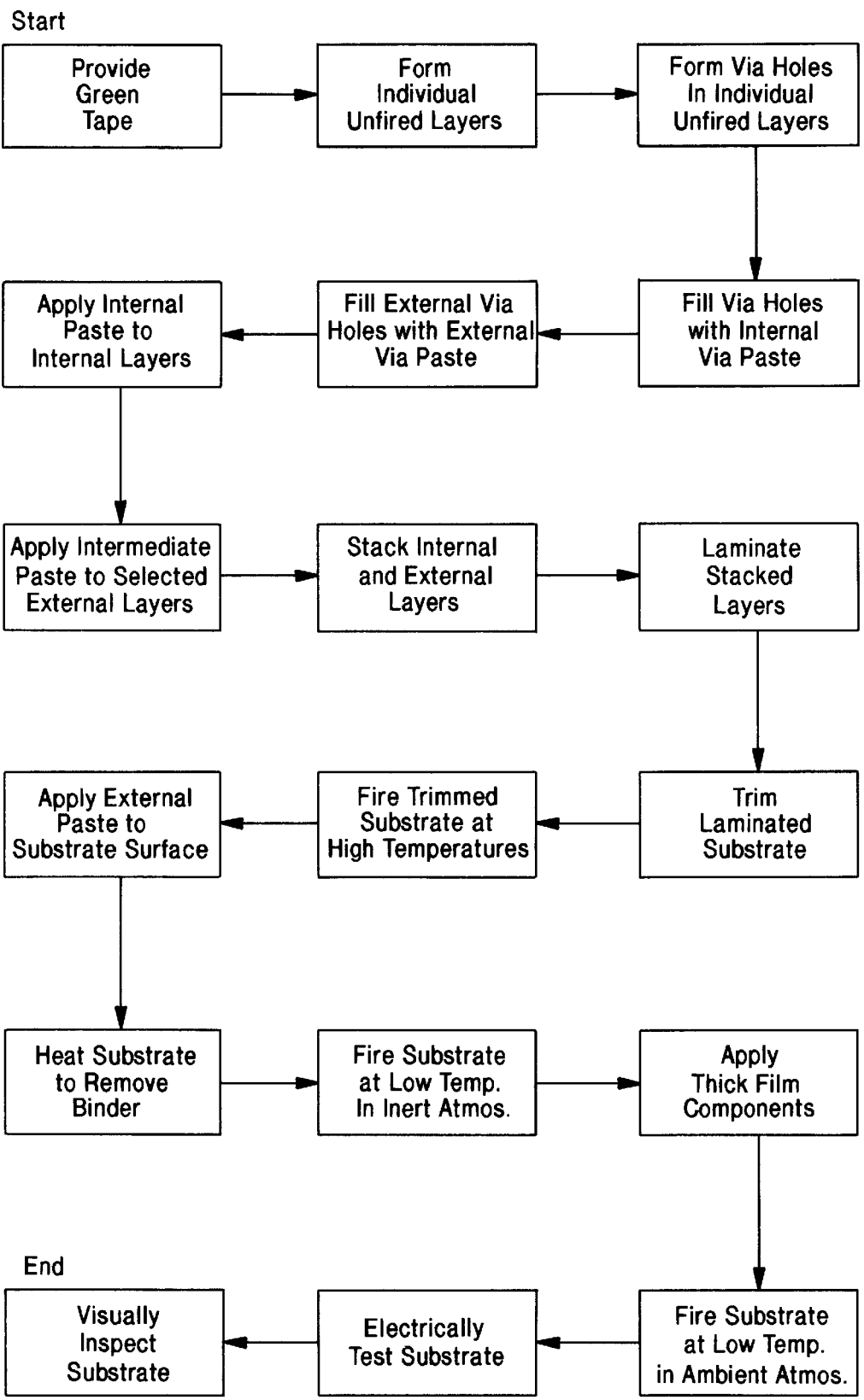
FIG. 8 shows a flow chart corresponding to one method of the present invention.

FIG. 8 shows a flow chart corresponding to one method of the present invention. The basic, preferred steps of the method shown in FIG. 8 may include the steps of:

(a) providing green tape or other suitable material for forming unfired ceramic layers therefrom;

(b) forming at least one unfired internal ceramic layer 71 and at least two unfired external ceramic layers 74 from the green tape or other suitable material;

(b) punching, or otherwise forming, via holes for internal vias 68 in the at least one unfired internal ceramic layer 71;

(c) punching, or otherwise forming, via holes for external vias 66 in at least one of the unfired external ceramic layers 74;

(d) filling the internal via holes of the unfired, internal ceramic layer 71 with an internal via paste;

(e) filling the external via holes of the unfired, external ceramic layers 74 with an external via paste, where the external via paste has no tungsten or molybdenum therein, and comprises ceramic powder and at least one metal selected from the group consisting of palladium, platinum, osmium, iridium, technetium, rhenium or rhodium;

(f) printing, or otherwise applying, an internal paste on at least one surface of each unfired, internal ceramic layer 71 to form at least one internal metallization layer or circuitry pattern 64 thereon;

(g) printing, or otherwise applying, an intermediate paste on at least one surface of at least one selected unfired, internal ceramic layer 71, where at least portions of the selected layer 71 will engage directly at least portions of an upper or lower surface of a selected external ceramic layer 74 after a ceramic substrate 50 has been formed in a subsequent stacking or laminating step, and where the intermediate paste is printed on or otherwise applied on top of a previously applied internal metallization layer or circuitry pattern 64, to form at least one intermediate metallization layer or circuitry pattern 62 thereon;

(h) stacking the plurality of ceramic layers 71 and 74 in a predetermined order or sequence to form an unfired stacked ceramic substrate 50;

(i) laminating the unfired, stacked substrate 50 to form an unfired, laminated ceramic substrate 50 having only external vias 66 exposed on upper surface 52 or lower surface 51 thereof;

(j) trimming the laminated substrate 50 to form an unfired, trimmed, ceramic substrate 50;

(k) firing, at high temperatures and in a reducing atmosphere, the trimmed ceramic substrate 50 in a high-temperature firing step to form a high-temperature fired ceramic substrate 50;

(l) printing, or otherwise applying, a first external paste on at least upper surface 52 or lower surface 51 of high-temperature fired ceramic substrate 50 to form at least one external metallization layer or circuitry pattern 70 or 72 thereon;

(m) removing at least some of any binder that may be present in the external paste by heating the high-temperature fired ceramic substrate 50;

(n) firing, at low temperatures and in an inert atmosphere, the high-temperature fired ceramic substrate 50 having disposed on at least upper surface 52 or lower surface 51 thereof at least one external metallization layer or circuitry pattern 70 or 72 to form a low-temperature fired ceramic substrate 50;

(o) repeating steps (l) through (n) hereinabove as many times as required by the substrate design at hand to apply wire bond, solder pad, pin pad or other electrical or electronic components such as resistors, capacitors or inductors onto upper surface 52, lower surface 51, or layer or pattern 70 or 72, using second or subsequent external pastes;

(p) firing, at low temperatures and in an air atmosphere, the low-temperature fired ceramic substrate to form an air-fired ceramic substrate 50;

(q) testing the electrical performance and characteristics of the air-fired ceramic substrate 50; and (r) visually inspecting the air-fired ceramic substrate 50.

The basic, preferred steps of the method shown in FIG. 8 are described in greater detail below.

The green tape of the present invention must be suitable for high temperature applications, and may be manufactured in accordance with the detailed method described below.

At least one unfired internal ceramic layer 71 and at least two unfired external ceramic layers 74 are formed from the green tape or other suitable material such as a custom-made ceramic tape. Most preferably, those unfired layers comprise rectangular or square sheets of green tape that measure about 5 and ½ inches wide by about 5 and ½ inches long by about 8–10 thousandths of an inch. The dimensions of such rectangular or square sheets may vary widely, depending on the application at hand. Likewise, the thickness of the sheets may vary widely between about 2 and about 30 thousands of an inch in preferred embodiments of the present invention. Each layer is a dielectric layer in a resulting ceramic substrate comprising a plurality of stacked, laminated and fired individual ceramic layers.

Via holes for internal vias 68 are punched or otherwise formed in the at least one unfired internal ceramic layer 71. Most preferably, a conventional via hole punch is employed in this step. Less preferably, a drilling machine or laser iS employed to form internal vias 68.

Via holes for external vias 66 are punched or otherwise formed in at least one of the unfired external ceramic layers 74. Most preferably, a conventional via hole punch is employed in this step. Less preferably, a drilling machine or laser is employed to form external vias 66.

Internal via holes in the at least one unfired, internal ceramic layer 71 are filled with an internal via paste. Filling of the internal via holes is preferably accomplished using conventional techniques well known in the art. As described in greater detail below, the preferred embodiment of the internal via paste of the present invention comprises about 85% by weight tungsten, molybdenum refractory powder, or alloys, mixtures or combinations thereof, and about 15% by weight pre-milled, high temperature ceramic powder.

External via holes in the at least one unfired, external ceramic layer 74 having external via holes formed therein, are filled with an external via paste. Filling of the external via holes is accomplished using conventional techniques well known in the art. As described in greater detail below, the preferred embodiment of the external via paste of the present invention comprises at least about 70% by weight by ruthenium refractory powder and about 30% by weight or less pre-milled, high temperature ceramic powder.

Metals other than ruthenium may less preferably be employed to form the external via paste of the present invention. For example, palladium, platinum, osmium, iridium, technetium, rhenium or rhodium may also be employed to form the external via paste of the present invention; provided, however, that the composition of the external via paste of the present invention is appropriately modified and adjusted. In the event a metal other than ruthenium is employed to form the external paste of the present invention, parameters requiring adjustment may include ceramic tape formulation, ceramic powder particle size, and the amounts of organic material or ceramic present in the paste.

The pre-milled high temperature ceramic powder employed in the internal and external via pastes of the present invention most preferably has a softening point ranging between about 1200° C. and about 1600° C., and comprises, in order of descending preference, between about 95% and 100%, between about 90% and 100%, between about 80% and 100%, between about 70% and 100%, and between about 50% and 100% aluminum oxide by weight An internal paste is screen printed or otherwise applied to at least one surface of each unfired, internal ceramic layer 71 to form at least one internal metallization layer or circuitry pattern 64 thereon. Such internal ceramic layers 71 are those layers having upper or lower surfaces that will not be exposed to, or otherwise brought in direct contact with, upper surface 52 or lower surface 51 of the resulting ceramic substrate 50. The screen printed internal paste forms refractory internal metallization layers or circuitry patterns 64 on the upper or lower surfaces of the individual unfired internal ceramic layers 71.

The internal paste of the present invention most preferably comprises tungsten or molybdenum, or an alloy, mixture or combination thereof, 15% by weight pre-milled ceramic powder, and a paste medium containing an organic binder. Molybdenum may also be used to replace tungsten in the internal paste of the present invention, or may be mixed with tungsten in the internal paste of the present invention. Organic binders such as ethyl cellulose are preferably present in the paste medium of the internal paste of the present invention. The organic binders impart an appropriate degree of cohesiveness and thickness or viscosity to the internal paste that facilitates screen printing or other processes where the internal paste is applied or deposited onto the surface of a ceramic layer or substrate. The organic binders are removed from the internal paste during the high-temperature firing process through volitalization or burning off.

In a preferred embodiment of the present invention, and before the high temperature firing step, the internal paste comprises about 85% by weight tungsten or molybdenum metal, or alloys, mixtures or combinations thereof, and about 15% by weight paste medium containing an organic binder; after the high-temperature firing step the fired internal paste contains no, or substantially no, organic binders because those binders have been driven off by the high temperatures of the high-temperature firing step.

A screen printer is most preferably employed to print the internal paste on individual, unfired internal ceramic layers 71. Other refractory metals suitable for use in the internal paste from which internal metallization layers or circuitry patterns 64 may be formed include iridium, osmium, palladium, platinum, rhenium, rhodium, ruthenium, technetium, and alloys, mixtures or combinations thereof, and other highly electrically conductive metals known to resist melting at high temperatures. Increased cost and lower electrical performance characteristics of the foregoing additional refractory metals may render them poor candidates, however, in respect of ruthenium, tungsten and molybdenum for making internal metallization layers or circuitry patterns 64 of the present invention.

An intermediate paste is screen printed or otherwise applied on at least one surface of at least one selected unfired, internal ceramic layer 71, where at least portions of the selected internal layer 71 will engage directly at least portions of an upper or lower surface of a selected external ceramic layer 74 after a ceramic substrate 50 has been formed in a subsequent stacking or laminating step. The intermediate paste may be printed on or otherwise applied on top of a previously applied internal metallization layer or circuitry pattern 64 to form at least one intermediate metallization layer or circuitry pattern 62 thereon. Alternativery and more preferably, the intermediate paste may be printed on or otherwise applied on the inner surface of external layer 74, such as the bottom surface of upper external layer 74 or the top surface of lower external layer 74, to form at least one intermediate metallization layer or circuitry pattern 62 thereon.

The intermediate paste of the present invention most preferably comprises a mixture of ruthenium and tungsten, no ceramic powder and a paste medium containing organic binders such as ethyl cellulose. Molybdenum may also be used to replace tungsten in the intermediate paste of the present invention, or may be mixed with tungsten in the intermediate paste of the present invention. The organic binders are removed from the intermediate paste during the high-temperature firing process through volitalization or burning off.

In a preferred embodiment of the present invention, and before the high temperature firing step, the intermediate paste comprises about 85% by weight of a mixture of tungsten and ruthenium, and about 15% by weight paste medium containing an organic binder; after the high-temperature firing step the fired intermediate paste contains no, or substantially no, organic binders because those binders have been driven off by the high temperatures of the high-temperature firing step.

A screen printer is most preferably employed to print the intermediate paste on selected, unfired internal ceramic layers 71. Other metals suitable for use in the intermediate paste from which intermediate metallization layers or circuitry patterns 62 may be formed include iridium, osmium, palladium, platinum, rhenium, rhodium, ruthenium, technetium, and alloys, mixtures or combinations thereof. Increased cost and lower electrical performance characteristics of at least some of the foregoing additional metals may render them poor candidates, however, in respect of ruthenium, tungsten and molybdenum for making intermediate metallization layers or circuitry patterns 62 of the present invention.

If metals other than ruthenium, tungsten and molybdenum are employed to form the intermediate paste of the present invention, the composition of the intermediate paste should most preferably be an alloy, mixture or combination of the metals contained in external via 66 and internal metallization layer 64. A preferred weight percent ratio of the metal present in internal metallization layer 64 to the metal present in external via 66 is about 70/30. Other weight ratios of those metals may less preferably be employed in the intermediate paste of the present invention, such as weight percent ratios of about 10/90, about 20/80, about 30/70, about 40/60, about 50/50, about 60/40, about 80/20, and about 90/10 of the metal present in internal metallization layer 64 to the metal present external via 66. Depending on the particular alloy, mixture or combination formulation selected for the intermediate paste of the present invention, it may also be desirable to adjust or change the amount of organic material present in the paste medium.

Unfired internal and external ceramic layers 71 and 74 are stacked one atop the other such that external layers 74 form upper surface 52 and lower surface 51 of resulting substrate 50 and at least one internal layer 71 is sandwiched between external layers 74. Moreover, layers 74 and 71 should be stacked in a predetermined order or sequence that is dictated by the requirements of the particular network design at hand. Resulting stacked layers 71 and 74 form an unfired stacked ceramic substrate 50. It is preferred that custom molds and plates well known to those skilled in the art be employed to stack individual, unfired ceramic layers 71 and 74 in the predetermined order to form unfired, stacked ceramic substrate 50.

Unfired, stacked ceramic substrate 50 is laminated to form an unfired, laminated ceramic substrate 50 having only external vias 66 exposed on upper surface 52 or lower surface 51 thereof. That is, no internal vias 68 or internal metallization layers or circuitry patterns 64 are exposed on, or in direct contact with, upper surface 52 or lower surface 51 of unfired, laminated ceramic substrate 50.

Ceramic substrate 50 is most preferably laminated isostatically using a solution pressurized Pacific Trinetics Corporation isostatic laminator. Ceramic substrate 50 is most preferably pre-sealed in a laminate bag, followed by the bag being placed in the laminator, the bag being pre-soaked for about 15 minutes at a lamination soaking temperature of 56 degrees C., and substrate 50 being laminated by compressive means for about 90 seconds. In the tenth step, it is preferred that a lamination adhesive, described below in greater detail, be disposed between individual unfired ceramic layers 71 and 74 prior to lamination.

Laminated substrate 50 is trimmed to form an unfired, trimmed, ceramic substrate 50. In the trimming step, ceramic substrate 50 is most preferably trimmed to a desired shape by employing a punch and die for notching laminated substrate 50, or by employing a heated knife to cut laminated substrate 50. After stacking, laminating and trimming substrate 50, only external vias 66 are exposed on upper surface 52 or lower surface 51 of resulting unfired, stacked, laminated and trimmed ceramic substrate 50.

In the high-temperature firing step of the present invention, trimmed ceramic substrate 50 is fired at high temperatures in a reducing atmosphere to form a high-temperature fired ceramic substrate. Firing in this step most preferably occurs at high temperatures between about 1400° C. and about 1800° C., where substrate 50 is subjected to such temperatures during the peak temperature portion or portions of the firing cycle. Temperature ranges that may be employed in the high temperature firing step include temperatures ranging between about 1450° C. and about 1750° C., between about 1500° C. and about 1700° C., and between about 1550° C. and about 1650° C.

In the high temperature firing step, it is preferred that substrate 50 enter an RTC or BTU brand kiln at an initial low temperature, and then be gradually heated to a peak temperature between about 1400° C., and about 1800° C. maintained at those temperatures during the peak temperature portion of the high temperature firing step, gradually cooled to lower temperatures, and then removed from the kiln. The preferred peak temperature during the high temperature firing step is about 1600° C., where substrate 50 is fired at that temperature for about 3 hours.

The duration of the peak temperature portion of the high-temperature firing step may range between about 5 minutes and about 8 hours in duration. More preferred durations of the peak temperature portion of the high-temperature firing step range between about 1 hour and 5 hours, and between about 2 hours and 4 hours.

In the high-temperature firing step of the present invention, peak temperatures of about 1420° C., about 1440° C., about 1460° C., about 1480° C., about 1500° C., about 1520° C., about 1540° C., about 1560° C., 1580° C., about 1600° C., about 1620° C., about 1640° C., about 1660° C., about 1680° C., about 1700° C., about 1720° C., about 1740° C., 1760° C., and about 1780° C. may be employed.

The preferred duration of the high-temperature firing step, which includes the peak temperature portion or portions thereof, is about 25 hours. Other suitable durations of the high temperature firing step of the present invention range between about 1 hour and 75 hours, between about 5 hours and 50 hours, between about 10 hours and 40 hours, and between about 20 hours and 30 hours. The duration of the high temperature firing step depends on many factors, including kiln load, belt speed, kiln peak temperature, and the amount and type of binder present in the green casting tape or paste material from which the unfired substrate 50 is formed.

It is preferred that the temperature and duration of the high-temperature firing step be sufficient to permit the internal and external vias and the internal metallization circuitry patterns to densify sufficiently that the migration of oxygen molecules into internal portions of the ceramic substrate is inhibited or prevented. Preventing such migration of oxygen molecules is especially important in the subsequent air firing step.

The reducing atmosphere of the high-temperature firing step is most preferably provided by a 3:1 mole ratio of hydrogen and nitrogen gas. Alternatively, the reducing atmosphere of the high-temperature firing step may be provided by hydrogen gas only, or any other single gas or mixture of gases capable of providing a reducing atmosphere where electrons are readily provided to ceramic substrate 50.

After the high-temperature firing step, it is highly desirable that external vias 66 not protrude above the plane formed by upper surface 52 or lower surface 51 of high-temperature fired ceramic substrate 50 to facilitate post-firing printing of external metallization layers or circuitry patterns 70 or 72. The addition of high temperature ceramic powder to the external via paste has been discovered to be an important factor in establishing optimum firing characteristics for external vias 66 of the present invention.

A first external paste is screen printed or otherwise applied on at least upper surface 52 or lower surface 51 of high-temperature fired ceramic substrate 50 to form at least one external metallization layer or circuitry pattern 70 or 72 thereon. External layer or pattern 70 or 72 is most preferably applied using a surface screen printing process and an AMI Screen Printer. External patterns or layers 70 or 72 are most preferably formed using a thick film process, but a thin film process may also be employed.

The first external paste of the present invention most preferably comprises gold, platinum-gold alloys, or other suitable thick film metallizations which contain inorganic low temperature binders. A preferred external thick film paste suitable for use in wire bonding applications of the present invention is Du Pont 5725Y paste containing gold. A preferred external thick film paste suitable for use in soldering applications of the present invention is ESL brand 5800B paste containing gold and platinum. Another suitable external thick film paste of the present invention is a two-stage system where Du Pont 9885Y and Du Pont 9596Y gold-platinum pastes are employed. In brazing applications, Du Pont 5062Y and 5063Y gold pastes are preferred for the external thick film paste of the present invention. It is further preferred that external layer or pattern 70 or 72 be formed of an external paste that contains no tungsten or molybdenum.

Depending upon the particular hybrid device requirements at hand, external metallization layer or pattern 70 or 72 may be formed from an external paste comprising a metal or metals other than gold or platinum and gold such as iridium, osmium, palladium, platinum alone, rhenium, rhodium, ruthenium, technetium, and alloys, mixtures or combinations thereof. Increased cost, lower electrical performance characteristics, and other qualities or characteristics of at least some of the foregoing additional metals may render them poor candidates, however, in respect of gold or platinum and gold for making external metallization layers or circuitry patterns 70 or 72 of the present invention.

After the at least one external metallization layer or pattern 70 or 72 is applied on at least upper surface 52 of lower surface 51 of substrate 50, it is preferred that any organic binder present in the external paste be removed by heating ceramic substrate 50 through a heating cycle or step where peak temperatures of about 525° C. are reached for about 25 minutes. A BTU Engineering Corporation furnace is preferred in the heating step. The heating step drives off undesirable volatile components that may be present in the binder of the external paste.

The first and subsequent external pastes are most preferably employed to form wire bond, solder pad or pin pad metallization layers 70 or 72 on upper or lower surfaces 52 or 51. The first and subsequent external pastes may also be employed to form at least one thick film electrical or electronic component such as a resistor, capacitor or inductor on external metallization layer or circuitry pattern 70 or 72. The various first, second, third, etc. external pastes may vary in composition or formulation from one to another.

Depending on the particular substrate design at hand, and after firing at low temperatures in an inert atmosphere but before air firing, second and subsequent external pastes may be individually: (a) applied to upper or lower surfaces 52 or 51, (b) heated to drive off volatile components in the organic binder, and (c) fired at low temperatures in an inert atmosphere. A wire bond metallization layer 70 or 72, for example, might be applied to upper or lower surface 52 or 51 using a first external paste, followed by heating to drive off lo volatile organic components in the first external paste and firing at low temperatures in an inert atmosphere. Then the external paste application, heating and low-temperature firing steps might be repeated by applying a second external paste to upper or lower surface 52 or 51 to form a solder pad metallization layer 70 or 72, followed by heating to drive off volatile organic components in the second external paste and firing at low temperatures in an inert atmosphere. A third external paste could be employed to form a pin pad external metallization layer 70 or 72 on surface 52 or 51, or to form electrical or electronic components such as resistors, capacitors or inductors on external metallization layer or circuitry pattern 70 or 72. The process loop comprising the steps of external paste application, heating and low-temperature firing may be repeated as many times as the particular substrate design at hand requires; provided, however, that substrate 50 is not air fired before those steps are completed, or alternatively all external vias are covered by fired metallization layers.

In the low-temperature firing step of the present invention, the high-temperature fired ceramic substrate 50, where substrate 50 may have disposed on at least upper surface 52 or lower surface 51 thereof at least one external metallization layer or circuitry pattern 70 or 72, is fired at low temperatures between about 600° C. and 1000° C. to form a low-temperature fired substrate 50. Most preferably, the low-temperature firing step of the present invention is carried out in an inert atmosphere.

In preferred embodiments of the present invention, the low-temperature firing step occurs at low temperatures between about 600° C. and about 1000° C., where substrate 50 is subjected to such temperatures during the peak temperature portion or portions of the low-temperature firing step. Temperature ranges that may be employed in the low-temperature firing step include temperatures ranging between about 650° C. and about 950° C., between about 700° C. and about 900° C., and between about 750° C. and about 850° C.

The preferred duration of the low-temperature firing step is about 40 minutes. The preferred peak temperature of the low temperature firing step is about 800° C., where substrate 50 is fired at that temperature for between about 30 seconds and about 10 minutes during the peak temperature portion of the air-firing step.

The duration of the peak temperature portion of the low-temperature firing step may also range between about 15 seconds and about 20 minutes in duration. More preferred durations of the peak temperature portion of the low-temperature firing step range between about 2 minutes and about 8 minutes, and between about 4 minutes and about 6 minutes.

In the low-temperature firing step, it is preferred that substrate 50 enter an RTC or BTU brand kiln at an initial low temperature, and then be gradually heated to a peak temperature between about 600° C. and about 1000° C., maintained at those temperatures during the peak temperature portion of the low-temperature firing step, gradually cooled to lower temperatures, and then removed from the kiln.

The low-temperature firing step may occur in a non-inert gas atmosphere; provided, however, that the thin or thick film external metallization layer or circuitry 70 or 72 is formed of a metal such as gold, platinum, copper or nickel, or alloys, mixtures or combinations thereof.

In the present invention, the low-temperature firing step, which includes the peak temperature portion or portions thereof, may have durations ranging between about 15 seconds and about 3 hours in duration. More preferred durations of the peak temperature portion of the low-temperature firing step range between about 5 minutes and about 2 hours, and between about 20 minutes and about 60 minutes. In the low-temperature firing step of the present invention, peak temperatures of about 620° C., about 640° C., about 660° C., about 680° C., about 700° C., about 720° C., about 740° C., about 760° C., about 780° C., about 800° C., about 820° C., about 840° C., about 860° C., about 880° C., about 900° C., about 920° C., about 940° C., about 960° C., and about 980° C. may be employed.

It was discovered that the low-temperature firing step of the present invention was desirable because it provided an improved mechanical bond exhibiting relatively low electrical resistance between external vias 66 and external metallization layers or circuitry patterns 70 or 72. It is preferred that such a low electrical resistance bond be established in the low-temperature firing step before the air firing step commence. An inert gas comprising $N_2$ molecules is preferred for forming the inert, non-reactive atmosphere of the low-temperature firing step. Other gases such as argon, helium, other suitable inert gas or even a vacuum may also be employed during the low-temperature firing step. For example, we expect that carbon dioxide may be employed successfully in the low-temperature firing step. Metals such as copper or nickel may also be employed to form external metallization layers 70 or 72 in the low-temperature firing step with an inert atmosphere.

At least one thick film electrical or electronic component such as a resistor, capacitor or inductor may be printed or otherwise applied on external metallization layer or circuitry pattern 70 or 72 of low-temperature fired substrate 50. In the present invention, thick film printing or component placement following the low-temperature firing step is aided by external metallization layers or circuitry patterns 70 or 72 not "posting" or having protrusions extending an excessive or undesirable height above surrounding upper surface 52 or lower surface 51 after the low-temperature firing step has been completed.

The air-firing step of the present invention preferably follows printing of any thin or thick film electrical components on external metallization layer or circuitry pattern 70 or 72 of low-temperature fired substrate 50. In the air-firing step, low-temperature fired ceramic substrate 50 is fired at low temperatures in an air atmosphere to form air-fired ceramic substrate 50. In preferred methods of the air firing step, the air-temperature firing step occurs at low temperatures between about 600° C. and about 1000° C., where substrate 50 is subjected to such temperatures during the peak temperature portion or portions of the air-firing step.

The most preferred peak temperature during the air temperature firing step is about 850° C., where substrate 50 is fired at that temperature for about 40 minutes. The duration of the peak temperature portion of the air-temperature firing step may also range between about 4 minutes and about 3 hours, between about 10 minutes and 2 hours, and between about 20 minutes and about 60 minutes.

In the air firing step, it is preferred that substrate 50 enter a BTu brand kiln at an initial low temperature, and then be gradually heated to a peak temperature between about 600° C. and about 1000° C., maintained at those temperatures during the peak temperature portion of the air-firing step, gradually cooled to lower temperatures, and then removed from the kiln. The air-firing step has been discovered to impart optimum characteristics to external metallization layers or circuitry patterns 70 or 72 disposed on upper surface 52 or lower surface 51.

In the air-firing step of the present invention, peak temperatures of about 620° C., about 640° C., about 660° C., about 680° C., about 700° C., about 720° C., about 740° C., about 760° C., about 780° C., about 800° C., about 820° C., about 840° C., about 860° C., about 880° C., about 900° C., about 920° C., about 940° C., about 960° C., and about 980° C. may be employed.

In the present invention, the duration of the air-firing step, which includes the peak temperature portion or portions thereof, may have durations ranging between about 4 minutes and about 5 hours in duration. More preferred durations of the peak temperature portion of the low-temperature firing step range between about 20 minutes and about 2 hours, and between about 40 minutes and about 80 minutes. The most preferred duration of the air firing step is about 60 minutes. The duration of the air-firing step depends on many factors, including kiln load, belt speed, kiln peak temperature, and the amount and type of binder present in the external paste of the present invention.

It is preferred that the electrical performance and electrical characteristics of air-fired ceramic substrate 50 be electrically tested after the air-firing step. Conventional electrical and electronic test equipment may be employed in the testing step. In the electrical testing step, the capacitance of individual metallization layers of patterns 70 or 72 disposed on surfaces 51 or 52 may be tested. Capacitance testing of substrate 50 may be performed using a TELEDYNE® TECHNISERVE® Model No. 4276A LCZ meter. Other electrical tests may also be performed on substrate 50.

Electrically tested air-fired ceramic substrate 50 is next visually inspected for defects. Typical defects looked for in substrate 50 include improper or missing surface prints, bumps in surface conductors or surfaces 51 or 52, and other undesired anomalies typically associated with ceramic hybrid packaging.

Finally, after electrical testing, and final visual inspection of the air-fired ceramic substrate 50, substrate 50 is ready for hybrid assembly. Since there is no, or substantially no, shrinkage variation associated with the external metallization circuitry patterns disposed on air-fired ceramic substrates 50 of the present invention, the present invention has been found to lend itself particularly well to flip chip substrate methods.

The reduction in shrinkage variation provided by the present invention also permits pad locations disposed along the outer periphery of the air-fired ceramic substrate 50 to be positioned more consistently and accurately from substrate to substrate, thereby enhancing the utility of the present invention in respect of flip chip applications. Air-fired ceramic substrate 50 of the present invention has also been discovered to lend itself particularly well to wire bonding or solder attachment of surface mount components thereto.

In preferred methods of the present invention, preparation of the green tape for forming individual ceramic layers of the present invention comprises the following steps. First, 61.3% ALCAN® calcined alumina powder, 3.0% AJAX® clay, 2.0% MISTRON® talc, 0.9% calcium carbonate, 20.0% toluene and 5.2% synasol, where the foregoing percentages are expressed in weight percent, are placed in a 52 gallon mill manufactured by U.S. STONEWARE® The various constituents in the mill are mixed and subsequently subjected to a conventional ball milling process for between about 2 and about 12 hours at room temperature to produce an intermediate green casting slurry. The intermediate green casting slurry is dried for about two hours, ±15 minutes, in a BLUE M® oven at about 125 degrees F., ±10 degrees F.

The resulting green tape slurry is combined in the mill with 4.7% BUTVAR-98® binder, 2.1% dibutyl pthalate, and 0.8% ucon oil, where the foregoing percentages are expressed in weight percent, and subsequently subjected to a conventional ball milling process for about 15 hours at room temperature to produce a castable green tape slurry. The castable green tape slurry is next passed through a tape caster machine having a doctor blade configuration to form an unfired green tape. As the unfired green tape material emerges from the casting tape machine, it is coated with a castable dielectric composition that upon firing at high temperatures forms a glass.

The preferred method of making foregoing castable dielectric composition comprises the following steps. First, 40.7% ALCAN calcined alumina powder, 2.0% AJAX clay, 4.1% MISTRON talc, 20.2% toluene, 13.4% ethanol, 0.5% KELLOX® Z-3 fish oil, 0.7% colloidal silica and 0.02% blue dye, where the foregoing percentages are expressed in weight percent, are placed in a 27 gallon mill manufactured by U.S. STONEWARE. The various constituents in the mill are mixed and subsequently subjected to a conventional ball milling process for several hours at room temperature to produce an intermediate castable dielectric material. The resulting slurry is combined in the mill with 8.9% SANTI-CIZER® 160 and 9.5% BUTVAR B-79 binder, and subsequently subjected to a conventional ball milling process at room temperature to produce the castable dielectric composition.

In a preferred method of the present invention, preparation of the internal via paste of the present invention comprises the following steps. Seven hundred and fifty grams of pre-milled ceramic powder having substantially the same formulation and made using substantially the same steps described above respecting green tape are blended with 4,250 grams of tungsten M-20 powder obtained from SYLVANIA®/OSRAM® of Towanda, Pa. in a HOBART® mixer having a wire whip for about 30 minutes. Six hundred grams of terpineol medium paste are next rolled for about 5 minutes on a jar mill roller before the paste medium is mixed at low speed using a standard mixing blade. The blended powders are next added to the paste medium in a mixer, where the blended powders are added to the paste medium at a rate of about two cups every 4 minutes until all blended powder has been added. After the paste and a high speed three-roll mill.

The medium paste is made by combining 2,120 grams of #318 terpineol with 330 grams of ethyl cellulose one teaspoon at a time in a mixer, mixing for about 20 minutes, and rolling the resulting mixture in a tightly closed container on a single tier roller for about 8 hours.

A different but similar medium paste is most preferably employed for tungsten BCA circuit print metallization, where 2,100 grams of dibutyl acetate are combined with 900 grams of ethyl cellulose using substantially the same mixing and rolling procedures described above respecting the medium paste employed in internal vias of the present invention.

In a preferred method of the present invention, preparation of a pre-milled ruthenium powder for forming the external via paste comprises the following steps. First, 300.8 grams of ruthenium powder passed through a 325 mesh, 250 grams of isopropanol, and 1200 grams of burundum ball media consisting of 87% alumina are mixed in a container that is subsequently subjected to a conventional ball milling process for about 12 hours to produce an intermediate ruthenium powder product. The intermediate ruthenium powder product is dried for about two hours, ±15 minutes, in a BLUE M® oven at about 125 degrees F., ±10 degrees F., to form the ruthenium powder of the present invention that is employed to form the external via paste of the present invention. Preferred particle sizes for the preferred ruthenium powder incorporated into the external via paste of the present invention are 2.75 microns ±0.75 microns, where 50% of the powder has an average particle size corresponding to such particle size specification.

In a preferred method of the present invention, preparation of a pre-milled ceramic powder for forming the external via paste of the present invention comprises the following steps. First, 912 grams of ALCAN alumina, 44 grams of AJAX "P" clay, 30 grams of MISTRON #400 talc, 13 grams of calcium carbonate and 666 grams of an RM9 mixture of ethanol/synasol are mixed in a container and that is subsequently subjected to a conventional ball milling process for about 24 hours to produce an intermediate ceramic powder product. The intermediate ceramic powder product is dried for about two hours, ±15 minutes, in a BLUE M® oven at about 125 degrees F., ±10 degrees F., and sifted in a SWECO® separator to form the ceramic powder of the present invention that is employed to form the external via paste of the present invention.

In a preferred method of the present invention, preparation of an external via paste of the present invention comprises the following steps. First, 220.8 grams of the above-described pre-milled ruthenium powder and 55.2 grams of the above-described pre-milled ceramic powder are mixed in a closed container that is subsequently subjected to a rolling process for about 5 minutes. Next, 33 grams taken from a mixture of 500 grams of #318 terpineol and 56 grams of T100 paste are added to the rolled and mixed ruthenium and ceramic powders along with 1.5 grams of #318 terpineol. The resulting paste is mixed thoroughly for several minutes in a mixer until clumps of dark gray clay-like material form. The resulting external via paste is then run through or processed in a small three-roll mill five times to ensure proper mixing.

In the laminating step described hereinabove, a low-temperature lamination adhesive is most preferably applied to the top or bottom surfaces of the individual ceramic layers to effect temporary bonding therebetween. A preferred lamination adhesive is formed by mixing 3000 grams of butyl cellulose acetate at low to medium speed in a container, and slowly adding small portions of 300 grams of polyvinyl buteral or BUTVAR B-79 binder to the butyl cellulose acetate until all binder has been added thereto. Mixing should continue for about 20 minutes, followed by rolling the resulting mixture on a single tier roller for about 3 hours.

Figure 9:
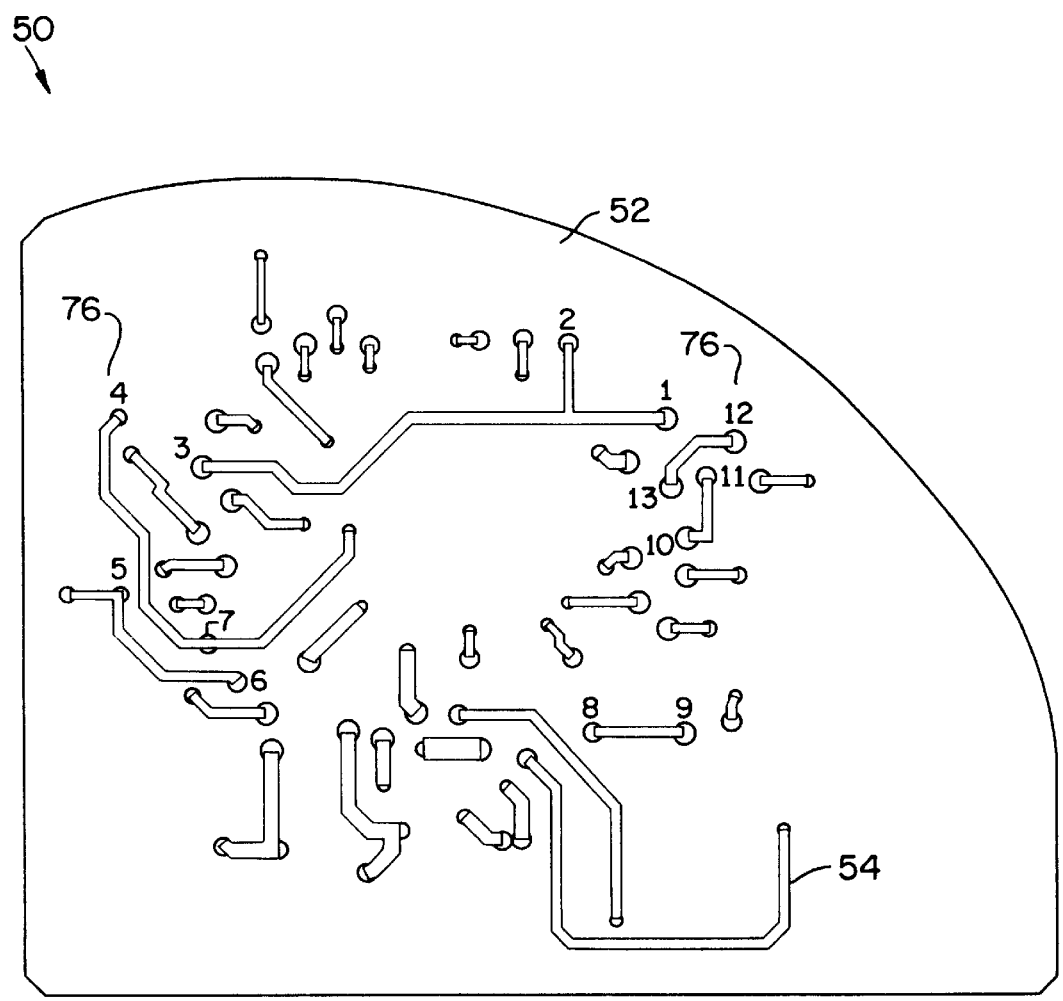
FIG. 9 shows the location of resistance test pads on ceramic substrates of the present invention and of the prior art.
Figure 10:
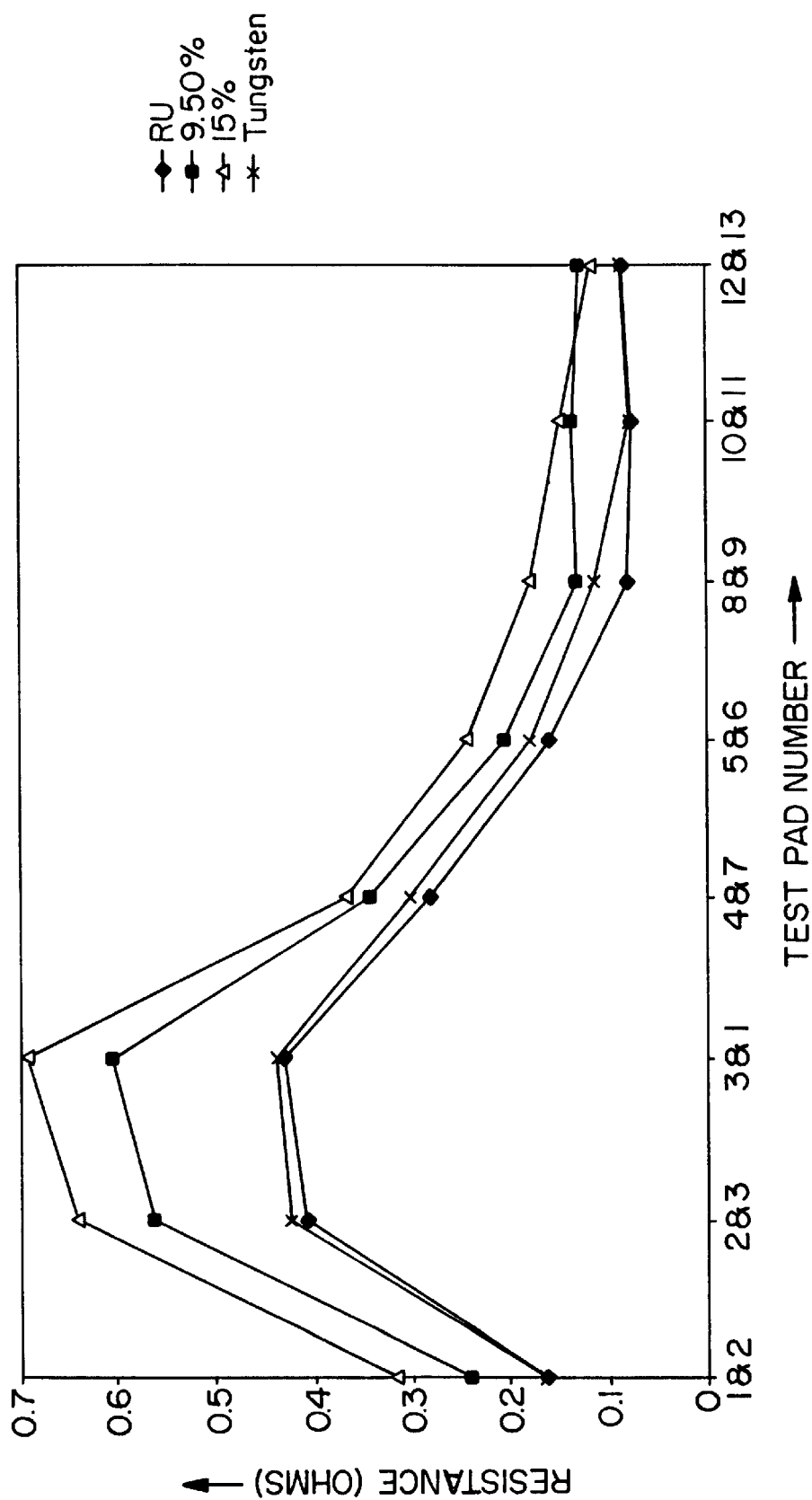
FIG. 10 shows a graph of resistance versus test pad location for ceramic substrates of the present invention after the high-temperature firing step and of the prior art, where the test pad configuration of FIG. 9 was employed.
Figure 11:
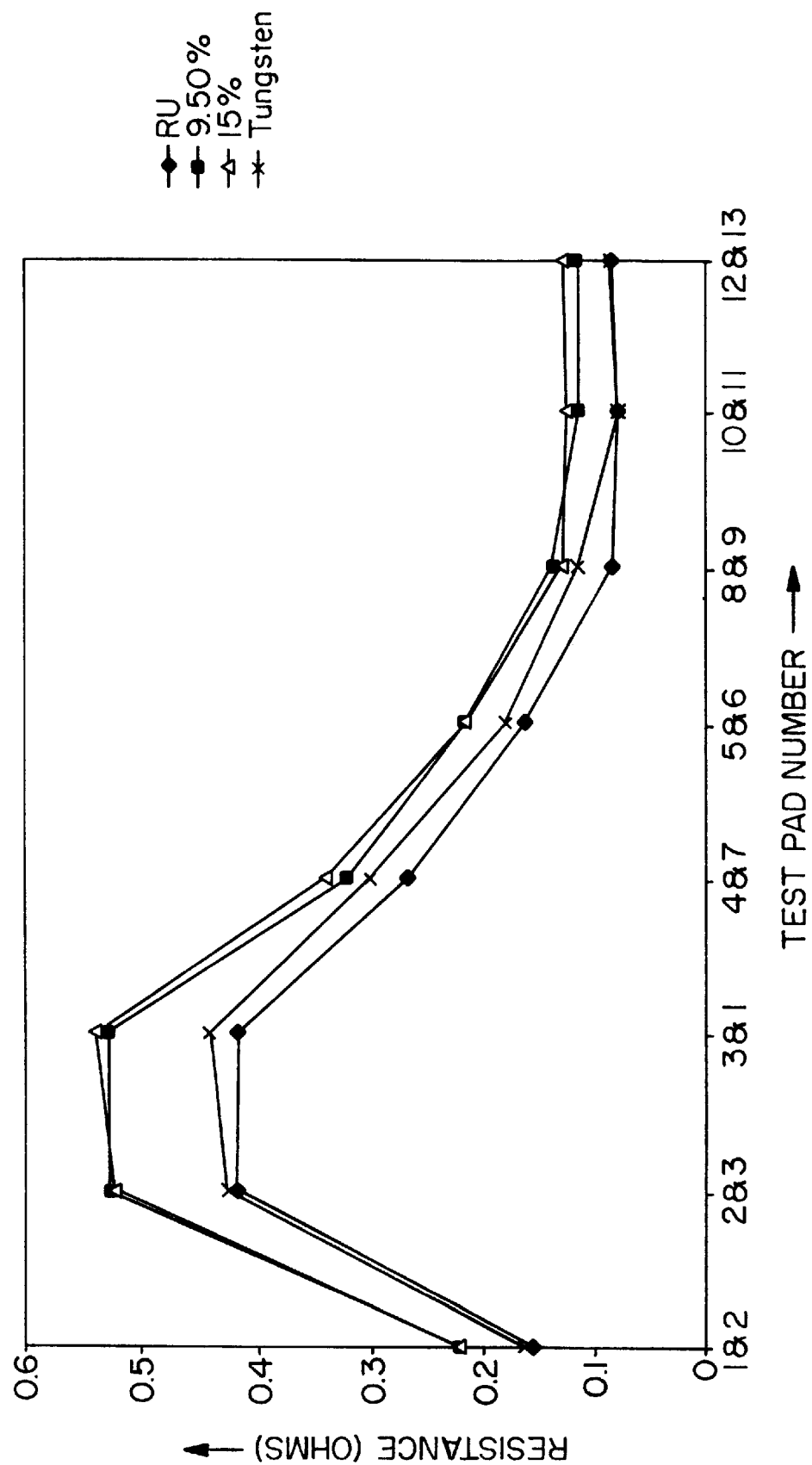
FIG. 11 shows a graph of resistance versus test pad location for ceramic substrates of the present invention after the air-firing step and of the prior art, where the test pad configuration of FIG. 9 was employed.

FIG. 9 shows the location of test pads on ceramic substrates 50 of the present invention and of the prior art employed to obtain the resistance data presented in FIGS. 10 and 11. Various ceramic substrates 50 of the present invention were formed along with a control ceramic substrate of the prior art for the purpose of ascertaining that substrates of the present invention provided acceptable resistance results. The prior art substrate contained vias and conductors formed from standard production tungsten paste containing 15% ceramic powder and tungsten surface metallization patterns subsequently plated with nickel and gold. Several different ceramic substrates 50 were formed using external via pastes of the present invention and gold thick film surface 100% ruthenium powder; (b) 9.5% ceramic powder and 91.5% ruthenium powder; and (c) 15% ceramic powder and 85% ruthenium powder.

FIG. 10 shows results obtained in substrates subjected only to the high-temperature and low-temperature firing steps. FIG. 11 shows the results obtained in substrates subjected to the high-temperature, low-temperature and air-firing steps. A gold print was screened onto top surfaces 52 of each of substrates 50 of the present invention following either the high-temperature or low-temperature firing step to electrically connect the networks shown in FIG. 9, and to permit resistances of the vias to be measured using a Hewlett-Packard Model No. HP3458A multimeter. Tungsten surface metallization patterns containing 15% ceramic powder disposed on top surface 52 of substrates 50 of the prior art, contrariwise, were plated first with nickel and then gold.

FIG. 10 shows a graph of resistance versus test pad location for ceramic substrates 50 of the present invention and of the prior art after the high-temperature and low-temperature firing steps, where the test pad configuration of FIG. 9 was employed. FIG. 10 shows that substrates 50 of the present invention provide acceptable resistance measurements less than 0.7 ohms in all cases. Measurements less than 6 to 7 ohms for such vias are generally considered acceptable by those skilled in the art. Table 2 below sets forth the specific resistance measurements obtained and shown in FIG. 10.

TABLE 2

Resistance vs. Test Pad Data Obtained After
High-Temperature and Low-Temperature Firing Steps

| Pads Tested | Ruthenium Only External Vias (ohms) | Ruthenium + 9.5% Ceramic External Vias (ohms) | Ruthenium + 15% Ceramic External Vias (ohms) | Tungsten External Vias (ohms) |
|---|---|---|---|---|
| 1 & 2 | 0.1553 | 0.2204 | 0.2228 | 0.165 |
| 2 & 3 | 0.4181 | 0.5241 | 0.5206 | 0.427 |
| 3 & 1 | 0.4180 | 0.5253 | 0.5356 | 0.441 |
| 4 & 7 | 0.2669 | 0.3229 | 0.3413 | 0.302 |
| 5 & 6 | 0.1631 | 0.2159 | 0.2160 | 0.180 |
| 8 & 9 | 0.0851 | 0.1380 | 0.1290 | 0.115 |
| 10 & 11 | 0.0801 | 0.1149 | 0.1255 | 0.080 |
| 12 & 13 | 0.0851 | 0.1153 | 0.1283 | 0.088 |

FIG. 11 shows a graph of resistance versus test pad location for ceramic substrates 50 of the present invention and of the prior art after the high-temperature, low-temperature and air-firing steps, where the test pad configuration of FIG. 9 was employed. FIG. 11 shows that substrates 50 of the present invention provide acceptable resistance measurements less than 0.6 ohms in all cases. Measurements less than 6 to 7 ohms for such vias are generally considered acceptable by those skilled in the art. Table 3 below sets forth the specific resistance measurements obtained and shown in FIG. 11.

TABLE 3

Resistance vs. Test Pad Data Obtained After High-Temperature,
Low-Temperature and Air-Firing Steps

| Pads Tested | Ruthenium Only External Vias (ohms) | Ruthenium + 9.5% Ceramic External Vias (ohms) | Ruthenium + 15% Ceramic External Vias (ohms) | Tungsten External Vias (ohms) |
|---|---|---|---|---|
| 1 & 2 | 0.1616 | 0.2393 | 0.3160 | 0.165 |
| 2 & 3 | 0.4106 | 0.5628 | 0.6414 | 0.427 |
| 3 & 1 | 0.4326 | 0.6048 | 0.6949 | 0.441 |
| 4 & 7 | 0.2818 | 0.3453 | 0.3691 | 0.302 |
| 5 & 6 | 0.1608 | 0.2046 | 0.2423 | 0.180 |
| 8 & 9 | 0.0814 | 0.1321 | 0.1795 | 0.115 |
| 10 & 11 | 0.0769 | 0.1374 | 0.1491 | 0.080 |
| 12 & 13 | 0.0859 | 0.1285 | 0.1190 | 0.088 |

Figure 12:
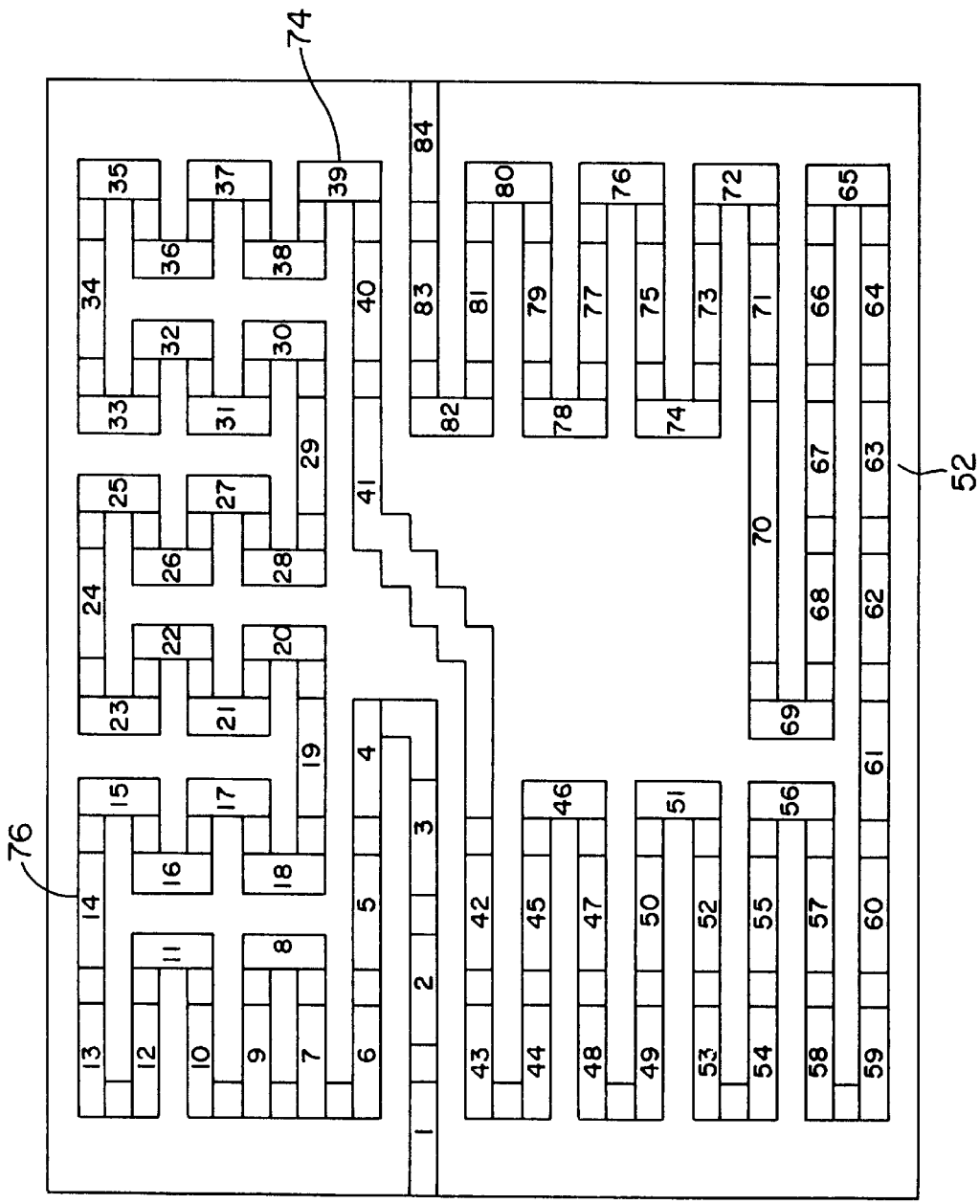
FIG. 12 shows the location of resistance test pads on ceramic substrates of the present invention and of the prior art.

FIG. 12 shows the location of test pads on daisy chain ceramic substrates 50 of the present invention and of the prior art. Ceramic substrates 50 of the present invention were formed along with control ceramic substrates 50 of the prior art for the purpose of ascertaining that the substrates of the present invention provided acceptable resistance results. In Tables 4 and 5, part number columns refer to part numbers of specific substrates tested, while resistance pad columns refer to electrical resistances measured between pad number 1 and pad number 41, pad number 1 and pad number 84, or pad number 41 and pad number 84 for substrates having the "daisy-chain" configuration shown in FIG. 13.

The prior art substrate contained vias and conductors formed from standard production tungsten paste and tungsten surface metallization subsequently plated with nickel and gold. Substrate 50 of the present invention was formed using an external via paste of the present invention and gold thick film surface metallization, where the external via comprised 20% ceramic powder and 80% ruthenium powder.

Figure 13:
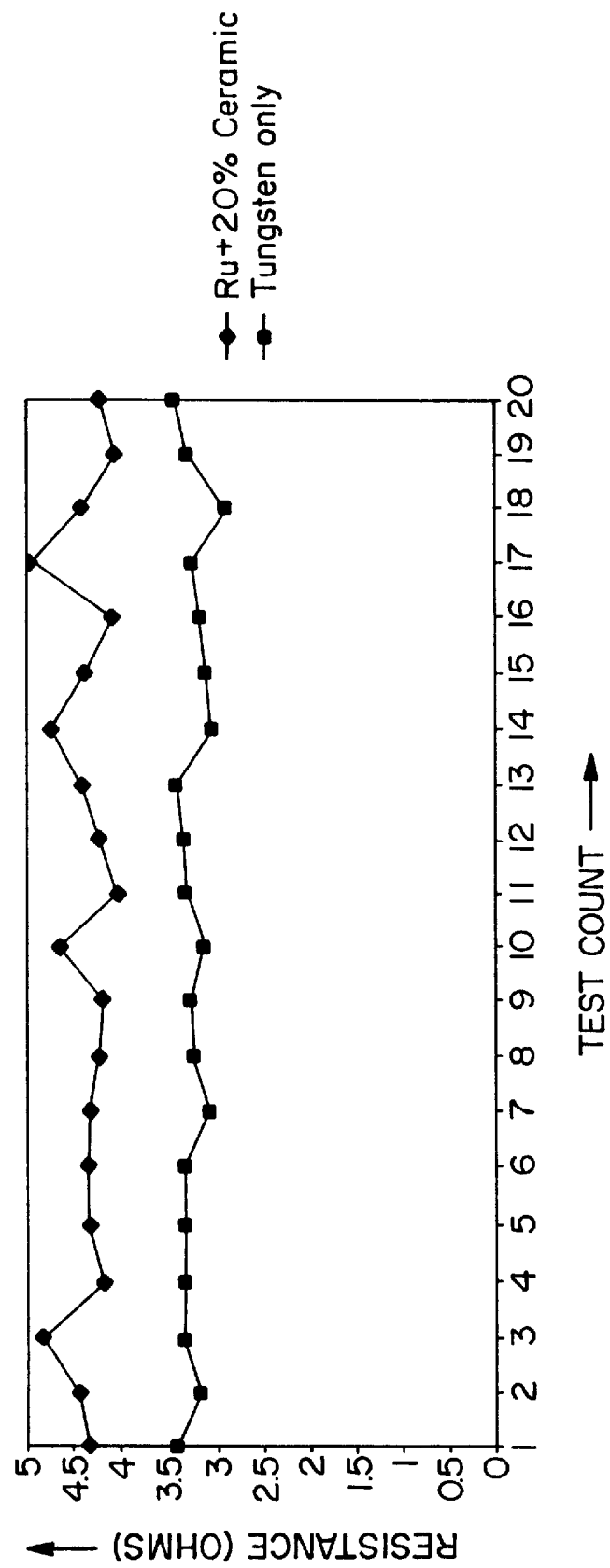
FIG. 13 shows a graph of resistance versus resistance test number for ceramic substrates of the present invention and of the prior art after the air-firing step, where the test pad configuration of FIG. 12 was employed.

FIG. 13 shows a graph of resistance versus test pad number for ceramic substrates 50 of the present invention and of prior art after the air-firing step, where the test pad configuration of FIG. 12 was employed. FIG. 13 shows that substrate 50 of the present invention provides acceptable resistance measurements less than about 5 ohms in all cases. Measurements less than 6 to 7 ohms for such vias are generally considered acceptable by those skilled in the art. Tables 3 and 4 below set forth specific and additional resistance measurements obtained, some of which are shown in FIG. 13.

TABLE 4

Prior Art Substrate Resistance vs. Test Pad Data

| | Resistance Pads Tested | | |
| --- | --- | --- | --- |
| Part Numbers | 1 TO 84 (ohms) | 1 TO 41 (ohms) | 41 TO 84 (ohms) |
| 1 | 3.43 | 1.63 | 1.80 |
| 2 | 3.19 | 1.52 | 1.67 |
| 3 | 3.35 | 1.59 | 1.77 |
| 4 | 3.34 | 1.57 | 1.77 |
| 5 | 3.34 | 1.55 | 1.79 |
| 6 | 3.34 | 1.56 | 1.78 |
| 7 | 3.09 | 1.44 | 1.65 |
| 8 | 3.24 | 1.52 | 1.73 |
| 9 | 3.28 | 1.53 | 1.75 |
| 10 | 3.15 | 1.50 | 1.66 |
| 11 | 3.32 | 1.59 | 1.73 |
| 12 | 3.35 | 1.58 | 1.78 |
| 13 | 3.42 | 1.62 | 1.80 |
| 14 | 3.06 | 1.42 | 1.65 |
| 15 | 3.13 | 1.45 | 1.69 |
| 16 | 3.20 | 1.52 | 1.68 |
| 17 | 3.28 | 1.55 | 1.73 |
| 18 | 2.92 | 1.35 | 1.57 |
| 19 | 3.32 | 1.57 | 1.75 |
| 20 | 3.46 | 1.63 | 1.84 |
| AVERAGE | 3.2605Ω | 1.5345Ω | 1.7295Ω |

TABLE 5

Resistance vs. Test Pad Data for the Present Invention

| | Resistance Pads Tested | | |
| --- | --- | --- | --- |
| Part Numbers | 1 TO 84 (ohms) | 1 TO 41 (ohms) | 41 TO 84 (ohms) |
| 1 | 4.33 | 2.04 | 2.28 |
| 2 | 4.44 | 2.11 | 2.32 |
| 3 | 4.83 | 2.33 | 2.49 |
| 4 | 4.17 | 2.00 | 2.15 |
| 5 | 4.32 | 2.08 | 2.22 |
| 6 | 4.33 | 2.06 | 2.26 |
| 7 | 4.31 | 2.05 | 2.25 |
| 8 | 4.22 | 2.02 | 2.19 |
| 9 | 4.16 | 1.96 | 2.19 |
| 10 | 4.65 | 2.23 | 2.41 |
| 11 | 4.03 | 1.91 | 2.11 |
| 12 | 4.22 | 2.00 | 2.21 |
| 13 | 4.4 | 2.04 | 2.34 |
| 14 | 4.74 | 2.23 | 2.49 |
| 15 | 4.37 | 2.08 | 2.28 |
| 16 | 4.1 | 1.91 | 2.15 |
| 17 | 4.94 | 2.00 | 2.57 |
| 18 | 4.4 | 2.04 | 2.30 |
| 19 | 4.08 | 1.93 | 2.13 |
| 20 | 4.21 | 2.03 | 2.17 |
| AVERAGE | 4.3625Ω | 2.0525Ω | 2.2755Ω |

Figure 14:
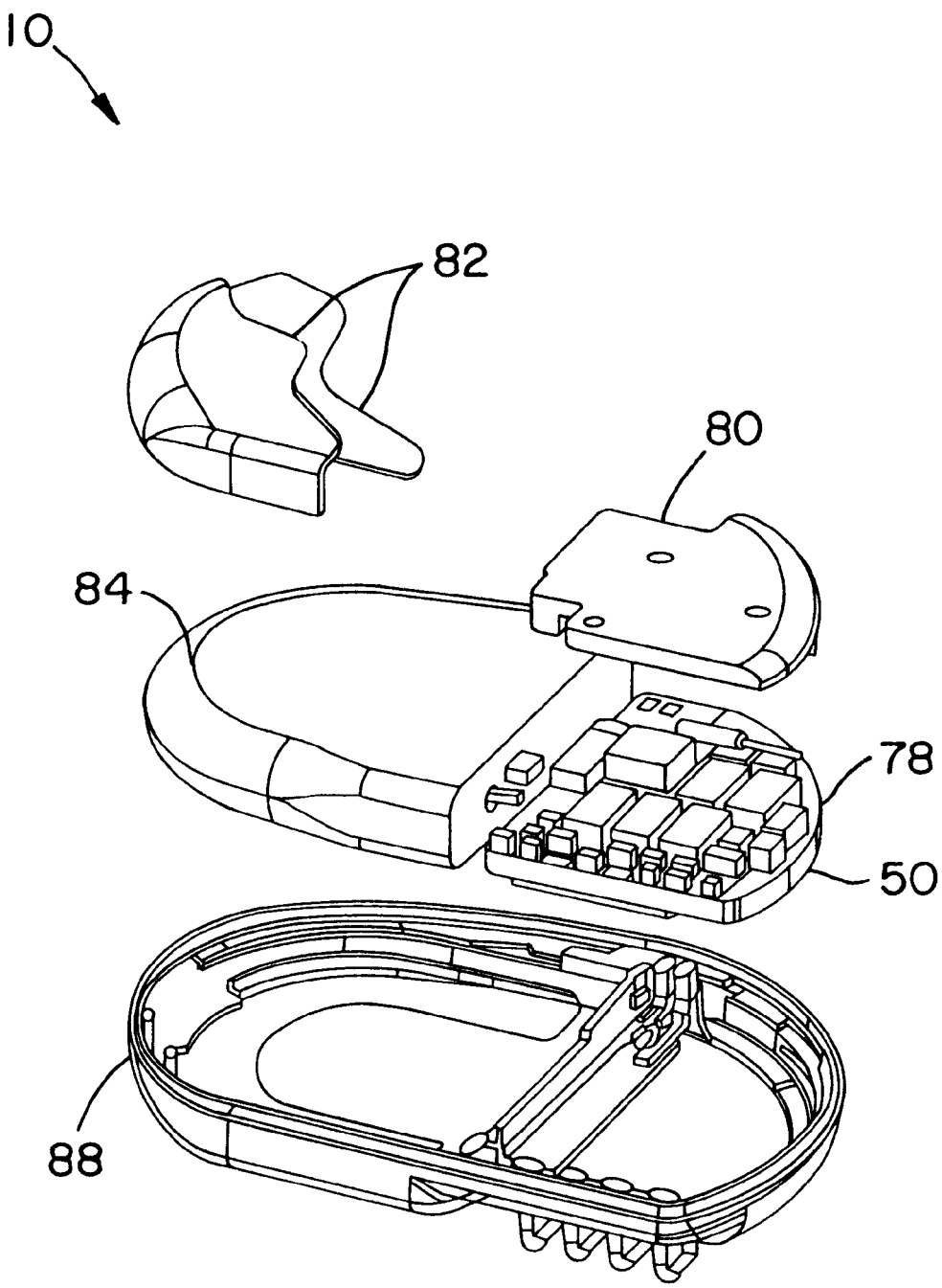
FIG. 14 shows an exploded view of an implantable medical device having one embodiment of the substrate of the present invention disposed therein.

FIG. 14 shows an exploded view of a portion of an implantable medical device having one embodiment of ceramic substrate 50 of the present invention disposed therein. Pacemaker 10 in FIG. 14 has ceramic substrate 50 of the present invention disposed therein. Substrate 50 has mounted on top surface 52 thereof various electronic components such as capacitors, an antenna and the like, which collectively form hybrid assembly 78. Dessicant shield or cover 80 and shield 82 are disposed atop hybrid assembly 78. Battery 84 provides power to hybrid assembly 78. Inner shield 88 receives battery 84 and hybrid assembly 78 therein. Other components such as a connector block, leads, an outer shield are not shown in FIG. 14.

Substrate 50 may be disposed in, and form an operative electronic component in the circuitry of, a pacemaker, a defibrillator, a PCD, an ICD, a neurological stimulator, a gastrointestinal stimulator and other implantable medical devices.

All papers, patents and publications listed in Table 1 or otherwise described above are incorporated by reference herein in their respective entireties. Additionally, U.S. patent appln. Ser. No. 08/632,730 entitled "Implantable Ceramic Enclosure for Pacing, Neurological and Application Specific Stimulation in the Human Body" to Hassler et a. filed Apr. 15, 1996 is hereby incorporated by reference herein in its entirety.

Although only a few exemplary embodiments and methods of the present invention have been described in detail above, those skilled in the art will appreciate readily that many modifications and other expedients known to those skilled in the art or disclosed herein are possible in the exemplary embodiments and methods without materially departing from the novel teachings and advantages of the invention. Accordingly, all such modifications are intended to be included within the scope of the present invention as defined in the following claims.

For example, methods falling within the scope of the present invention do not require that all steps recited hereinabove or shown in FIG. 8 be practiced. Some steps of the present invention recited hereinabove or shown in FIG. 8 may be practiced in an order or sequence different from that described or shown herein and nevertheless fall within the scope of the present invention. Moreover, steps in addition to those recited hereinabove or shown in FIG. 8 may be practiced in conjunction with some or all of the steps recited hereinabove or shown in FIG. 8 and nevertheless fall within the scope of the present invention.

The scope of the present invention is not limited to ceramic substrates for hybrid assemblies in implantable medical devices such as pacemakers or defibrillators, but includes ceramic substrates for feedthrough assemblies, connector blocks, enclosures, and housings in implantable medical devices.

The scope of the present invention is not limited to implantable medical device applications, but extends to all electronic hybrid packaging applications and methods. The scope of the present invention is not limited to implantable medical device applications where human organs are sensed or stimulated, but includes similar applications in other mammalians and mammalian organs. Additionally, the scope of the present invention is not limited to implantable medical device applications where a human or mammalian heart is sensed, monitored, paced, or defibrillated, but includes neurological, gastrointestinal and other applications.

The present invention includes within its scope a method of implanting an implantable medical device comprising the steps of surgically implanting the medical device in one of a human being and a mammalian subject to effect electrical stimulation of an organ, organs or portion of the organ therein, and telemetrically, magnetically, electrically or manually enabling the implanted medical device so that it may electrically stimulate the organ, organs or portion of the organ. The implantable medical device of the foregoing method may be a pacemaker, a defibrillator, a PCD, an ICD, a neurological stimulator or a gastro-intestinal stimulator.

We claim:

1. A method of manufacturing a ceramic substrate comprising the steps of:

(a) forming at least three unfired ceramic layers from green tape or an equivalent material, wherein at least one of the at least three unfired ceramic layers is an internal layer, and wherein two of the at least three unfired ceramic layers are first and second external layers, the first external layer forming an external upper surface of the substrate, the second external layer forming an external lower surface of the substrate;

(b) forming via holes in the at least one internal layer and in at least one of the external layers;

(c) filling the via holes of the at least one internal layer with an internal via paste;

(d) filling the via holes of at least one of the external layers with an external via paste, the external via paste having no tungsten or molybdenum therein, the external via paste comprising ceramic powder and at least one metal selected from the group consisting of palladium, platinum, osmium, iridium, technetium, rhenium, rhodium and ruthenium, and alloys, mixtures and combinations thereof;

(e) applying an internal paste to at least one of an upper surface and a lower surface of at least one internal layer to form at least one internal refractory metallization circuitry pattern thereon;

(f) applying an intermediate paste to the internal refractory metallization circuitry pattern on the internal layer and to the inner surface of the first or second external layer, where at least portions of the internal layer having the intermediate paste applied thereon engage directly at least portions of the inner surface of the first or second external layer, to form an intermediate metallization circuitry pattern thereon;

(g) stacking the at least one internal layer and the external layers such that the at least one internal layer is interposed between the upper external layer and the lower external layer to form an unfired stacked ceramic substrate;

(h) laminating the unfired, stacked ceramic substrate to form an unfired, laminated ceramic substrate having only external vias exposed on the upper and lower surfaces thereof;

(i) trimming the laminated ceramic substrate to form an unfired, trimmed, ceramic substrate;

(j) firing, at high temperatures and in a reducing atmosphere, the trimmed ceramic substrate in a high-temperature firing step to form a high-temperature fired ceramic substrate;

(k) applying to at least one of the upper external surface and the lower external surface at least one thick-film external surface metallization circuitry pattern to form a high-temperature fired ceramic substrate having at least one thick film external surface metallization circuitry pattern applied thereon;

(l) firing, at low temperatures and in an inert atmosphere, the high temperature fired ceramic substrate to form a low-temperature fired ceramic substrate, and (m) firing, at low temperatures and in an air atmosphere, the low temperature fired ceramic substrate to form an air-fired ceramic substrate.

2. A method of manufacturing a ceramic substrate, the substrate having at least three layers, at least one of the at least three layers being an intehial layer, two of the at least three layers being first and second external layers, the first external layer forming an external upper surface of the substrate, the second external layer forming an external lower surface of the substrate, and at least one of the external layers having via holes, comprising the steps of:

(a) applying an internal paste to at least one of an upper surface and a lower surface of at least one internal layer to form at least one internal refractory metallization circuitry pattern thereon, (b) applying an intermediate paste to at least one of the upper surface of the at least one internal layer, the lower surface of the at least one internal layer, and the inner surface of the first or second external layers, where at least portions of an at least one internal layer having the intermediate paste applied thereon engage directly at least portions of the least one external layer, to form at least one intermediate metallization circuitry pattern thereon which serves as a barrier to migration of metal from the internal metallization pattern;

(c) firing, at high temperatures and in a reducing atmosphere, the ceramic substrate in a high temperature firing step to form a high-temperature fired ceramic substrate; and (d) firing, at low temperatures and in an air atmosphere, the high-temperature fired ceramic substrate to form an air-fired ceramic substrate.

* * * * *

UNITED STATES PATENT AND TRADEMARK OFFICE
CERTIFICATE OF CORRECTION

PATENT NO.    : 6,284,080B1
DATED         : September 4, 2001
INVENTOR(S)   : Samel F. Haq, Patrick F. Malone and Donald P. Varner It is certified that error appears in the above-identified patent and that said Letters Patent is hereby corrected as shown below:

<u>Column 28,</u>
Line 16, delete "intehial" and insert -- internal --

Signed and Sealed this

Twenty-eighth Day of January, 2003

JAMES E. ROGAN
*Director of the United States Patent and Trademark Office*